United States Patent
Witchger, Jr. et al.

(10) Patent No.: US 12,299,166 B2
(45) Date of Patent: May 13, 2025

(54) METHODS, SYSTEMS AND COMPUTER PROGRAM PRODUCTS FOR HANDLING DATA RECORDS USING AN APPLICATION PROGRAMMING INTERFACE (API) AND DIRECTORY MANAGEMENT SYSTEM

(71) Applicant: Translational Imaging Innovations, Inc., Hickory, NC (US)

(72) Inventors: Andrew J. Witchger, Jr., Durham, NC (US); Robert C. Williams, Durham, NC (US); Alexander E. Salmon, Garner, NC (US); Maureen E. Tuffnell, Wauwatosa, WI (US); Taylor M. Szeto, Cary, NC (US); Tammy B. Carrea, Raleigh, NC (US); Eric L. Buckland, Hickory, NC (US)

(73) Assignee: Translational Imaging Innovations, Inc., Hickory, NC (US)

( * ) Notice: Subject to any disclaimer, the term of this patent is extended or adjusted under 35 U.S.C. 154(b) by 355 days.

(21) Appl. No.: 17/870,317

(22) Filed: Jul. 21, 2022

(65) Prior Publication Data
US 2023/0023922 A1  Jan. 26, 2023

Related U.S. Application Data

(60) Provisional application No. 63/224,503, filed on Jul. 22, 2021.

(51) Int. Cl.
*G06F 21/62* (2013.01)
*G06F 16/25* (2019.01)
(Continued)

(52) U.S. Cl.
CPC ........ *G06F 21/6245* (2013.01); *G06F 16/258* (2019.01); *G16H 30/20* (2018.01); *G16H 30/40* (2018.01)

(58) Field of Classification Search
CPC ............ G06F 21/6218; G06F 21/6245; G06F 16/258; G06F 16/284; G06H 30/20;
(Continued)

(56) References Cited

U.S. PATENT DOCUMENTS 5,237,626 A   8/1993  Forslund et al.
5,452,375 A   9/1995  Rousseau et al.
(Continued)

OTHER PUBLICATIONS

Sharing Clinical Trial Data: Maximizing Benefits, Minimizing Risk—Appendix B: Concepts and Methods for De-identifying Clinical Trial Data, Institute of Medicine of The National Academies, 2015.*

(Continued)

*Primary Examiner* — Christopher C Harris
(74) *Attorney, Agent, or Firm* — Stanek Lemon Crouse & Meeks, PA

(57) ABSTRACT

An application programming interface (API) resident on a computer is provided that, upon receiving a message that a data set associated with an encounter experienced by a subject is available, causes a processor to read a structured file associated with the data set, the structured file having a set of records assigned to a subset of pre-defined fields and a location of one or more unstructured objects, the pre-defined fields being organized according to an ontology having at least records related to the subject, the encounter and the data set; and populate at least first and second independent and distinct relational databases using endpoints of the API. The first relational database excludes records associated with the subject and the encounter and the second relational database includes records associated with the subject and the encounter. The second relational database includes multiple tables that can be accessed by invoking the API.

19 Claims, 15 Drawing Sheets

(51) Int. Cl.
*G16H 30/20* (2018.01)
*G16H 30/40* (2018.01)

(58) Field of Classification Search
CPC ........ G06H 30/40; G16H 10/20; G16H 30/20; G16H 30/40
See application file for complete search history.

(56) References Cited

U.S. PATENT DOCUMENTS

| | | | |
|---|---|---|---|
| 5,606,365 | A | 2/1997 | Maurinus et al. |
| 5,694,227 | A | 12/1997 | Starkweather |
| 6,028,611 | A | 2/2000 | Anderson et al. |
| 6,101,502 | A | 8/2000 | Heubner et al. |
| 6,747,702 | B1 | 6/2004 | Harrigan |
| 6,834,282 | B1 | 12/2004 | Bonneau et al. |
| 6,907,474 | B2 | 6/2005 | Oshins et al. |
| 6,950,985 | B2 | 9/2005 | Lee |
| 7,206,789 | B2 | 4/2007 | Hurmiz et al. |
| 7,373,600 | B2 | 5/2008 | Lee et al. |
| 7,441,182 | B2 | 10/2008 | Beilinson et al. |
| 7,716,246 | B2 | 5/2010 | Pepin |
| 7,978,888 | B2 | 7/2011 | Holmstrom |
| 8,330,772 | B2 | 12/2012 | Cote et al. |
| 8,401,257 | B2 | 3/2013 | Izatt et al. |
| 8,743,229 | B2 | 6/2014 | Kim |
| 8,782,601 | B2 | 7/2014 | Whitney et al. |
| 8,903,760 | B2 | 12/2014 | DeVries et al. |
| 9,106,713 | B2 | 8/2015 | Bell |
| 9,218,569 | B2 | 12/2015 | Dimitrijevic |
| 9,317,930 | B2 | 4/2016 | Kuo et al. |
| 9,928,339 | B2 | 3/2018 | Tolle et al. |
| 10,194,091 | B2 | 1/2019 | Nashizawa |
| 10,684,919 | B2 | 6/2020 | Ukis et al. |
| 10,970,468 | B2 | 4/2021 | Beechuk et al. |
| 11,042,696 | B2 | 6/2021 | Higinbotham |
| 11,094,404 | B2 | 8/2021 | Orosco et al. |
| 2008/0016111 | A1 | 1/2008 | Keen |
| 2011/0119088 | A1 | 5/2011 | Gunn et al. |
| 2013/0291060 | A1 | 10/2013 | Moore |
| 2016/0378919 | A1 | 12/2016 | McNutt et al. |
| 2018/0129684 | A1* | 5/2018 | Wilson ................ G06F 16/254 |
| 2019/0252052 | A1 | 8/2019 | Von Reden |
| 2019/0265971 | A1 | 8/2019 | Behzadi et al. |
| 2019/0287686 | A1 | 9/2019 | Takeda |
| 2020/0043600 | A1 | 2/2020 | Glottmann et al. |
| 2020/0251216 | A1 | 8/2020 | Schulte et al. |
| 2021/0158933 | A1 | 5/2021 | Frosch et al. |
| 2021/0193297 | A1 | 6/2021 | Buckland et al. |

OTHER PUBLICATIONS

Moore et al., De-identification of Medical Images with Retention of Scientific Research Value, Radiographics, 2015; 35: 727-735.*
International Search Report and Written Opinion dated Nov. 10, 2022, for PCT/US2022/037823 which has an International filing date of Jul. 21, 2022; 8 pages.
Final Office Action for U.S. Appl. No. 11/136,941, mailing date Mar. 12, 2010, 12 pages.

* cited by examiner

FIG. 1

| | | |
|---|---|---|
| TII_DICOM | SYSTEM | 303 |
| TII_DICOM | OBJECTS | 303 |
| APPLICATION | INSTITUTION | 305 |
| APPLICATION | DEPARTMENT | 305 |
| APPLICATION | LABORATORY | 305 |
| APPLICATION | DEVICE_STATION | 305 |
| APPLICATION | PERSONNEL_TYPE | 305 |
| APPLICATION | PERSONNEL | 305 |
| APPLICATION | STUDY | 305 |
| APPLICATION | PROJECT | 305 |
| APPLICATION | TIMEPOINT | 305 |
| APPLICATION | TREATMENT_ARM | 305 |
| APPLICATION | SUBJECT_TYPE | 305 |
| APPLICATION | SUBJECT | 305 |
| APPLICATION | SUBJECT_CODED | 305 |
| APPLICATION | SUBJECT_pii | 305 |
| APPLICATION | ENCOUNTER_TYPE | 305 |
| APPLICATION | ENCOUNTER | 305 |
| APPLICATION | VISIT | 305 |
| APPLICATION | PROCEDURE_TYPE | 305 |
| APPLICATION | PROCEDURE | 305 |
| APPLICATION | DEVICE_mfr | 305 |
| APPLICATION | DEVICE_BRAND | 305 |
| APPLICATION | DEVICE_MODEL | 305 |
| APPLICATION | DEVICE_INSTANCE | 305 |
| ocuVAULT | ACQUISITION_TYPE | 307 |
| ocuVAULT | ACQUISITION | 307 |
| ocuVAULT | DEVICE_CONFIGURATION_STATE | 307 |
| ocuVAULT | SUBSYSTEM_CONFIGURATION_SYSTEM | 307 |
| ocuVAULT | COMPONENET_CONFIGURATION_STATE | 307 |
| ocuVAULT | CHANNEL_TYPE | 307 |
| ocuVAULT | CHANNEL | 307 |
| ocuVAULT | CAPTURE_TYPE | 307 |
| ocuVAULT | CAPTURE | 307 |
| ocuVAULT | DEVICE_SETTINGS | 307 |
| ocuVAULT | SUBSYSTEM_SETTINGS | 307 |
| ocuVAULT | COMPONENT_SETTINGS | 307 |
| ocuVAULT | FILE_OBJECT_TYPE | 307 |
| ocuVAULT | FILE_OBJECT | 307 |

| | |
|---|---|
| 10 TII DICOM DICTIONARY | |
| 11 TII DICOM DICTIONARY OBJECT MODELS | |
| 10 TII APPLICATION INSTITUTION | |
| 11 TII APPLICATION DEPARTMENT | |
| 12 TII APPLICATION LABORATORY | |
| 13 TII APPLICATION DEVICE_STATION | |
| 14 TII APPLICATION PERSONNEL_TYPE | |
| 15 TII APPLICATION PERSONNEL | |
| 16 TII APPLICATION STUDY | |
| 17 TII APPLICATION PROJECT | |
| 18 TII APPLICATION TIMEPOINT | |
| 19 TII APPLICATION TREATMENT_ARM | |
| 1a TII APPLICATION SUBJECT_TYPE | |
| 1b TII APPLICATION SUBJECT | |
| 1c TII APPLICATION SUBJECT_CODED | |
| 1d TII APPLICATION SUBJECT_Pii | |
| 1e TII APPLICATION ENCOUNTER_TYPE | |
| 1f TII APPLICATION ENCOUNTER | |
| 20 TII APPLICATION VISIT | |
| 21 TII APPLICATION PROCEDURE_TYPE | |
| 22 TII APPLICATION PROCEDURE | |
| 23 TII APPLICATION DEVICE_mfr | |
| 24 TII APPLICATION DEVICE_BRAND | |
| 25 TII APPLICATION DEVICE_MODEL | |
| 26 TII APPLICTION DEVICE_INSTANCE | |
| 10 TII ocuVAULT ACQUISITION_TYPE | |
| 11 TII ocuVAULT ACQUISITION | |
| 12 TII ocuVAULT DEVICE_CONFIGURATION_STATE | |
| 13 TII ocuVAULT SUBSYSTEM_CONFIGURATION_STATE | |
| 14 TII ocuVAULT COMPONENT_CONFIGURATION_STATE | |
| 15 TII ocuVAULT CHANNEL_TYPE | |
| 16 TII ocuVAULT CHANNEL | |
| 17 TII ocuVAULT CAPTURE_TYPE | |
| 18 TII ocuVAULT CAPTURE | |
| 19 TII ocuVAULT DEVICE_SETTINGS | |
| 1a TII ocuVAULT SUBSYSTEM_SETTINGS | |
| 1b TII ocuVAULT COMPONENT_SETTINGS | |
| 1c TII ocuVAULT FILE_OBJECT_TYPE | |
| 1d TII ocuVAULT FILE_OBJECT | |

FIG. 9

METHODS, SYSTEMS AND COMPUTER PROGRAM PRODUCTS FOR HANDLING DATA RECORDS USING AN APPLICATION PROGRAMMING INTERFACE (API) AND DIRECTORY MANAGEMENT SYSTEM

CLAIM OF PRIORITY

The present application claims the benefit of and priority to U.S. Provisional Application Ser. No. 63/224,503, filed on Jul. 22, 2021, the content of which is hereby incorporated by reference as if set forth in its entirety.

GOVERNMENT CONTRACT

This inventive concept was made with government support under Grant No. 1R44EY031198 awarded by the National Institute of Health. The government has certain rights in the inventive concept.

BACKGROUND

The management of medical images and data in the context of research and clinical trials is notoriously difficult even as the opportunities and demand for imaging biomarkers and artificial intelligence clinical decision support systems is rapidly expanding. Successful development, validation, and clinical deployment of imaging biomarkers requires vast amounts of images supported by accurate clinical annotations. In the domain of artificial intelligent (AI) and big data, there is an urgency to deploy image and data management platforms that are Findable, Accessible, Interoperable, and Reusable (FAIR). This gets complicated in a multi-vendor, multi-modal, multi-site environment that lacks unified standards on imaging systems, metadata, and observational records.

A successful image management platform that addresses the needs of imaging biomarker development will be quite differentiated from a more traditional medical imaging Picture Archiving and Communications System (PACS). PACS systems are designed around access and visualization of images under well-defined conditions and are most suited to clinical diagnostic applications. While PACS system development has made significant advances in network availability and visualization, integration with observational medical records remains a challenge, and PACS systems are generally not suited to the management and analysis of populations of images in the big data and AI context.

A successful platform for the collection and utilization of images in the modern context must address the needs of diverse stakeholders, from research, to clinic, to patient. The unstructured, semi-structured, and structured data that makes up the medical imaging and health record environment must be easily findable by administrators and researchers alike, with appropriate security and respect of individual privacy rights. The data must generally be Accessible at the granularity required for specific tasks, and in such time frames as appropriate to various image-driven workflows. The images must be Interoperable across vendors, and appropriately interoperable across interrelated, correlated, or causal modalities. Images and data must generally then be reusable. Data definitions must generally be standard enough to be reused from study to study in the capture of new data, specific enough capture details required in complex medical domains, broad enough to be extensible to new domains of inquiry.

Clinical trials require aggregation of volumes of data from a multiplicity of examination devices, acquired on a large cross section of patients at often large number of clinical trial sites. Data quality, traceability, and security are essential in the collection, transport, and analysis of clinical trial data.

Clinical trials rely on combinations of biomarkers and endpoints to validate therapeutic safety and efficacy before regulatory bodies. The onus of developing robust, objective clinical trial endpoints places additional demands on the data management. Clinical trial endpoints are often developed in parallel with the pharmaceutical development and clinical trial process. Novel endpoints may be exploratory, without direct bearing on a regulatory decision, or secondary, as an adjunct to a primary definitive endpoint. In general, regulatory bodies seek structural endpoints, functional endpoints, and endpoints that directly tie to activities of daily living.

As the eventual primary or secondary endpoints may evolve through development and clinical trial process, it is particularly important to institute a robust data management process early, and systematically collect and organize exam data and exam metadata from the beginning, to maximize the usability to answer new questions that arise through the development lifecycle.

SUMMARY

Some embodiments of the present inventive concept provide an application programming interface (API) resident on a computer that, upon receiving a message that a data set associated with an encounter experienced by a subject is available, causes a processor to: read a structured file associated with the data set, the structured file having a set of records assigned to a subset of pre-defined fields and a location of one or more unstructured objects, the pre-defined fields being organized according to an ontology having at least records related to the subject, the encounter and the data set; and populate at least first and second independent and distinct relational databases using endpoints of the API, the first relational database including records related to the one or more unstructured objects and excluding records associated with the subject and the encounter and the second relational database including records associated with the subject and the encounter. A schema of the second relational database includes at least a first addressable table that includes protected data associated with the subject and the encounter and at least a second addressable table that excludes protected data associated with the subject and the encounter. A set of addressable processes of the API are invoked to export one or more of: unstructured objects and structured data about objects from the first relational database, the structured data being completely absent of records associated with the subject and the encounter; unstructured objects and structured data about objects from the first and/or second relational databases, the structured data including records associated with the encounter but being completely absent of records associated with the subject; and unstructured objects and structured data about objects from the first and/or second relational databases, the structured data including records associated with the subject and the encounter.

Related method, systems and computer program products are also provided.

BRIEF DESCRIPTION OF THE DRAWINGS

FIG. 1 is a block diagram illustrating a data ontology in accordance with some embodiments of the present inventive concept.

FIG. 9 is a table listing DICOM tags used in accordance with some embodiments of the present inventive concept.

DETAILED DESCRIPTION OF EMBODIMENTS

Figure 2:
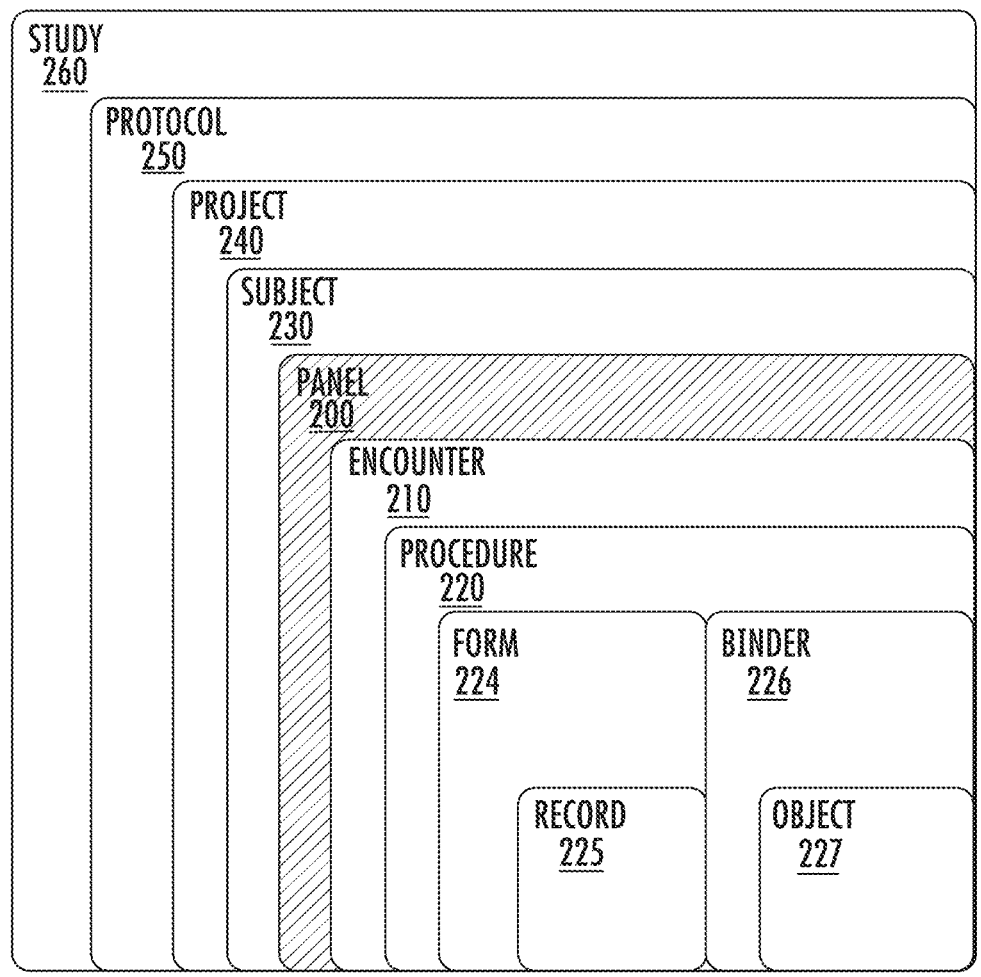
FIG. 2 is a nested block diagram illustrating the scope of observational data maintained within the data ontology in accordance with some embodiments of the present inventive concept.

The inventive concept now will be described more fully hereinafter with reference to the accompanying drawings, in which illustrative embodiments of the inventive concept are shown. This inventive concept may, however, be embodied in many different forms and should not be construed as limited to the embodiments set forth herein; rather, these embodiments are provided so that this disclosure will be thorough and complete, and will fully convey the scope of the inventive concept to those skilled in the art. Like numbers refer to like elements throughout. As used herein, the term "and/or" includes any and all combinations of one or more of the associated listed items.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

As will be appreciated by one of skill in the art, the inventive concept may be embodied as a method, data processing system, or computer program product. Accordingly, the present inventive concept may take the form of an entirely hardware embodiment or an embodiment combining software and hardware aspects all generally referred to herein as a "circuit" or "module." Furthermore, the present inventive concept may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices.

Computer program code for carrying out operations of the present inventive concept may be written in an object-oriented programming language such as Java®, Smalltalk or C++. However, the computer program code for carrying out operations of the present inventive concept may also be written in conventional procedural programming languages, such as the "C" programming language or in a visually oriented programming environment, such as VisualBasic or JavaFx.

The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The inventive concept is described in part below with reference to a flowchart illustration and/or block diagrams of methods, systems and computer program products according to embodiments of the inventive concept. It will be understood that each block of the illustrations, and combinations of blocks, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

As discussed in the background of the present inventive concept, the management of medical images and data in the context of research and clinical trials is notoriously difficult even as the opportunities and demand for imaging biomarkers and artificial intelligence clinical decision support systems is rapidly expanding. Meeting the demands of image-driven innovation and clinical care in the era of big data and artificial intelligence (AI) generally requires a comprehensive ontology that covers the medical imaging domain from hardware definition to observation records, from subject to image, from anatomy to disease. The ontology must be supported by methods to store records and images, move images and data from devices to storage to application, methods to rapidly curate, visualize, and annotate images, trace the provenance of images and data through algorithm development and validation, maximize the sharing of images and data over space and time, and protect the rights of access and use of individual patient data as required both ethically and legally. Accordingly, some embodiments of the present inventive concept provide an application programming Interface (API) and directory management system for organizing and managing data records in a database and objects in a "data lake" that provides ontology needed for big data and AI as will be discussed further herein.

Figure 12:
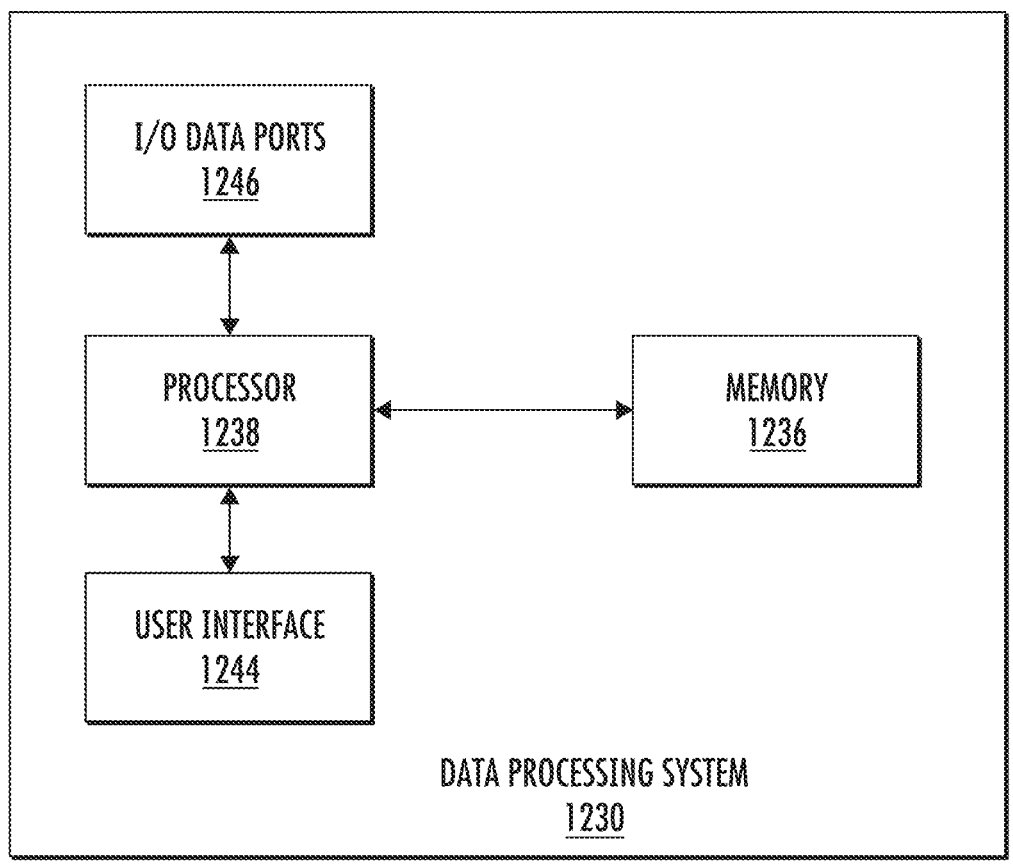
FIG. 12 is a block diagram of a high level data processor that can be used in accordance with some embodiments of the present inventive concept.

As used herein, AI refers to the simulation of human intelligence processes by machines, especially computer systems. Specific applications of AI include expert systems, natural language processing, speech recognition and machine vision. Some embodiments of the present inventive concept include a machine learning/AI component. The machine learning component can implement machine learning algorithms or artificial intelligence (AI) to generate and/or update neural networks that are executed by a processor (FIG. 12). In some embodiments, the machine learning component can use one or more machine learning algorithms to generate one or more models or parameter functions for the detections. The machine learning component can be configured to generate an event model that understands which types of data indicate which types of detections. One or more of these event models may be used to determine an expected value or occurrence based on analysis of received data. In some embodiments, criteria can be designated by a user, admin, or automatically. By designating specific types of detections, resources (e.g., processing power, bandwidth, etc.) can be preserved for only the types of detections desired.

Various types of algorithms may be used by the machine learning component to generate the output desired. For example, certain embodiments herein may use a logistical regression model, decision trees, random forests, convolutional neural networks, deep networks, or others. However, other event detection models are possible, such as a linear regression model, a discrete choice model, or a generalized linear model.

Some non-limiting examples of machine learning algorithms that can be used herein can include supervised and non-supervised machine learning algorithms, including regression algorithms (such as, for example, Ordinary Least Squares Regression), instance-based algorithms (such as, for example, Learning Vector Quantization), decision tree algorithms (such as, for example, classification and regression trees), Bayesian algorithms (such as, for example, Naive Bayes), clustering algorithms (such as, for example, k-means clustering), association rule learning algorithms (such as, for example, A priori algorithms), artificial neural network algorithms (such as, for example, Perceptron), deep learning algorithms (such as, for example, Deep Boltzmann Machine), dimensionality reduction algorithms (such as, for example, Principal Component Analysis), ensemble algorithms (such as, for example, Stacked Generalization), and/or other machine learning algorithms.

These machine learning algorithms may include any type of machine learning algorithm including hierarchical clustering algorithms and cluster analysis algorithms, such as a k-means algorithm. In some cases, the performing of the machine learning algorithms may include the use of an artificial neural network. By using machine-learning techniques, copious amounts (such as terabytes or petabytes) of received data may be analyzed to generate models without manual analysis or review by one or more people.

An API refers to a way for two or more computer programs to communicate with each other. It is a type of software interface, offering a service to other pieces of software. A document or standard that describes how to build or use such a connection or interface is called an API specification. A data lake refers to a centralized repository that allows you to store all structured and unstructured data at any scale.

Figure 1:
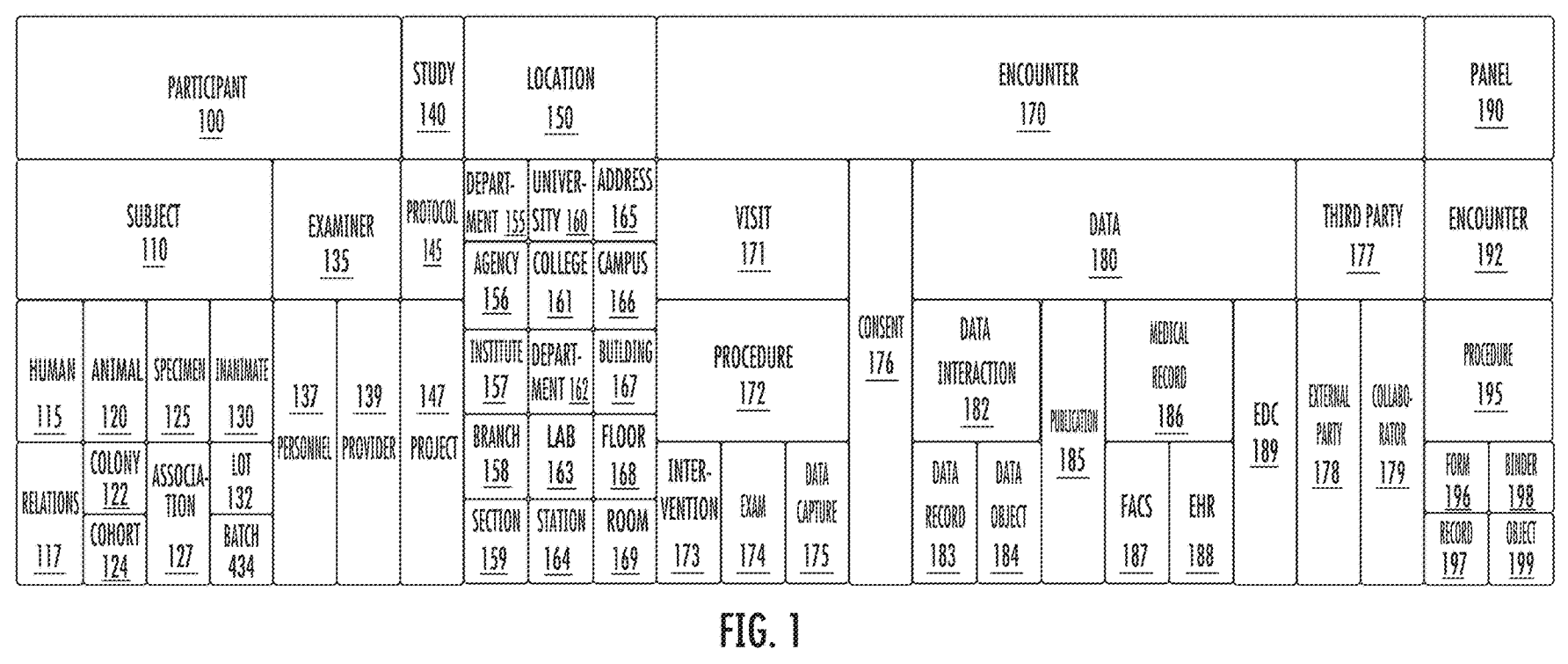

As further used herein, ontology refers to a set of concepts and categories in a subject area or domain that shows their properties and the relations between them. In the present inventive concept, the ontology refers to a hierarchical organization of entities that capture the data associated with a medical research program, clinical trial, or clinical evaluation, as illustrated in, for example, FIG. 1. At the top level of the hierarchy, data entities are organized by a set of entities that define the circumstances under which data is managed, a set of entities that define the data itself.

In this context, entities that define data management include entities that capture the creation of source data, for example through an examination of a patient or other subject, the movement of source data, and the access of source data, as will be defined further below.

In this context, entities that define the management of data includes entities that define Participant 100, Study 140, Location 150 and Encounter 170. A Participant may be the subject of a source data generating procedure or may be associated directly or indirectly with managing the generation of source data from a subject. In our ontology, Subject 110 is divided into four categories: human subject 115, animal subject 120, a specimen 125 derived from an animate subject, and inanimate subject 130. The human entity is paired with an entity defining relations 117. The animal entity is paired with a colony 122 and the colony may be divided into cohorts 124. Specimens are paired with an Association 127 to parent subject. Inanimate object may be associated with a Lot 132 and the lot may be divided into batches 134.

The group defining participants that are not the subjects are identified broadly as Examiner 135, and the Examiner entity is again separated into Personnel 137 and Provider 139. Personnel can be any person involved in any role associated with managing a procedure, and the roles are defined by a Type table associated with Personnel. The Provider entity provides the record of responsible individuals who receive, review, consult, or otherwise hold a position of accountability for the subjects and their procedures. A Provider may, for example be a clinician or a principal investigator, and the type of Provider may be further specified in a Type table.

The Study 140 entity contains the definition of a set of examinations or investigations, which may include one or more subjects and one or more procedures that generate source data. The Study is divided into a set of Protocols 145, and. Protocols are further divided into a set of Projects 147. The heart of the definition resides in the Protocol entity. The Protocol entity defines the set of required or allowed procedures, the inclusion and exclusion criteria of subjects, the roles and permissions of personnel associated with examinations or investigations. Projects are further segmentations of protocols that support the separation of responsibilities and workflows and provides finer granularity in the management of source-data provenance.

Workflows are managed through the Encounter 170 entity. The Encounter entity is further divided to manage multiple workflows important to management of Participants and Studies. The first workflow is the Visit 171 entity. The Visit provides for a set of Procedures 172 that are scheduled or performed at a specific point of time or stage of a Project (or Protocol or Study). Procedures are further sub-divided into interventions 173, Exams 174, and Data Capture 175. Interventions refer to a class of actions undertaken with respect to a Subject prior to the Exam. The Exam is the activity that generates results that are the target of the Procedure. Data Capture is the specific activity for preparing, securing, transporting, or storing the records associated with the Exam. A separate workflow entity is the Consent 176 entity. The Consent entity manages the set of documents, approvals, permissions, or constraints that may be required by the Project (Protocol or Study) for the conduct of the Visit, as well as access rights to the source data generated during a Visit. The Consent entity is vital to management of Personally Identified Information (PII), Protected Health Information (PHI), and maintaining compliance to Health insurance Portability and Accountability Act (HIPAA) in the United States and general data protection regulation (GDPR) in the European Union.

The Encounter entity also includes the following workflow management entities: Communications (not shown), Third Party 177, and Data 180 workflow entities. The communications entity provides structures for managing general communications, such as email, phone calls, facsimile, and the like. The Third Party 177 entity provides the structure for managing interactions with a) Collaborators 179, and b) External parties 178. As the name suggest, the Collaborator entity provides a structure for managing encounters with other parties who support an investigation or study that are outside of the primary group of Participants. External Party 178 encounters provide structure for managing encounters with, for example, auditors or regulatory bodies who in some way interact with the investigation or its source data.

The Encounter entity 170 provides a specific construction for managing interactions with source Data, including data derived from a Procedure and recorded at the time of Data Capture as well as other sources of data as described below. The data model further provides traceability of interactions with the Data through the Data Interaction 182 construct. The Data Interaction construct is divided to organize interactions with structured Data Records 183, such as protected or unprotected Subject metadata, and the unstructured Data Objects 184, such as image files. The data encounter log includes access, modifications, copies and transfers of source data, organized by records (fields that can be written into a database or file) and objects (images and documents and the like). The data encounter also manages inflows and outflows from external electronic medical records systems 186, included Picture Archiving and Communications System (PACS) 187 and electronic health records (HER) 188 Systems, as well an inflows and outflows from other Electronic Data Capture (EDC) 189 systems that may be feeders or receivers of data. Additionally, the data encounter provides an entity for Publications 185, in order to trace the provenance of data into documentation.

A Location 150 entity is used to manage the organization and geographic location of activity. A parallel construct is maintained to separate organization for geography. For example, as shown in FIG. 1, we may have multiple types of Institutions with unique hierarchies. A government agency may be defined by Department 155, Agency 156, Institute 157, Branch 158, and Sector 159. An academic institution may be defined by University 160, College 161, Department 162, Lab 163, and Station 164. A physical location may include an Address 165, Campus 166, Building 167, Floor 168, and Room 169.

The aforementioned entities of the ontology describe the who (Participant), what and when (Encounter), where (Location), and why and how (Study). The observational output in this ontology is managed through a generalized Panel 190. A Panel describes a set of observational records and objects derived from an exam that is part of Procedure undertaken for a Subject (by an Examiner). The Procedure 195 occurs during an Encounter 192 (for example, Visit), as part of a Project, defined by a Protocol that is part of a Study. For any given Procedure, a Form 196 is maintained to capture observational records 197, and a Binder 198 is maintained to capture source objects 199. The intent of the present inventive concept is that Forms and Binders are managed electronically, however they may be managed physically, copied and scanned into the data structure, or referenced by an electronic address to a physical location. The provenance of source data from its origin is maintained through the Participant, Study, Location and Encounter entities, where the Encounter Entities trace the forward flow of source data through Data Encounter entity (so long as the record is maintained within the platform).

The scope of a Panel is a feature of the present inventive concept. A Panel may start as a template, and the template is fully implemented in the context of a project fulfilling the requirements of a protocol as part of a study. As a record, a Panel will generally be specific to a subject (though one may envision a circumstance where a panel is recorded for a group), may span multiple encounters, with one or more procedures, one or more forms, and one or more binders, as illustrated in, for example, FIG. 2.

As illustrated in FIG. 2, a Panel 200 is a set of one or more observations derived from a Procedure 220 during an Encounter 210. Each Procedure 220 may have one or more structured observations, or records 225, that may be recorded on a Form 224, where the Form 224 may be an electronic record in a database. Each Procedure may also result in unstructured objects 227 such as images, which are abstracted to reside in binders 226, which may be electronic storage, PACS systems, Vendor Neutral Archives, and the like.

Panels are reusable and nestable constructs that define a set of target observations from reproducible examinations.

Panels may be constructed at the lowest level of a single procedure with a single observational record or may be more complex constructs. Panels may likewise be built up of other panels. Thus, Panels form traceable data constructs within the data ontology of the present inventive concept, or Genes of the Data Genome (as discussed below). As further noted in FIG. 2, Panels with observations are unique to Subjects 230 (though a Group may be a Subject if so defined).

A further hierarchy is introduced to manage the inherent complexity of biomedical research. A Study 260 is a top-level construct that may guide a multi-year, multi-site endeavor, for example, a Study may focus on the genetic origins of Glaucoma. In living subjects research, specific experimental forays into the Study are defined by Protocols 250 that are generally reviewed and approved by Institutional Review Boards (IRB) or the like. A single protocol may allow for extended investigative branches, or Projects 240. The encounters then of Subjects 230 are thus in the context of a Project 240 defined within a Protocol 250 inside of a larger Study 260. This construct provides significant flexibility within a controlled system required for living subjects research. Other hierarchies may be applied without deviating from the intent of the present inventive concept.

It will be understood that the details illustrated in and discussed above with respect to FIGS. 1 and 2 are provided for example only and embodiments of the present inventive concept are not limited thereto.

The unstructured, semi-structured, and structured data that makes up the medical imaging and health record environment is very important to clinical and research development. As one of skill in the art understands, being able to access this data and manipulate it is very important for both the present treatment of patients as well as for developing new treatments for the future. To further complicate use of this data, patients are entitled to anonymity and thus all personal data must be stripped from the remaining data before this data can be shared, searched, manipulated etc. Accordingly, some embodiments of the present inventive concept provide an API that has a two-sided database. It will be understood that more than two sides may be implemented without departing from the scope of the present inventive concept. A first side of the database (A-side or Record-side) includes metadata describing the Subject, Encounter, Study and the like, as well as metadata describing the Exam and the Data captured during the Exam. The second side of the database (B-side or object-side data lake) includes information describing Data, for example image objects and all metadata associated with the image, but excludes identifying data/information associated with the Subject. Thus, the data on the B-side may be manipulated, searched, shared etc. without any concern for confidentiality, except the extent that an object itself is considered to be itself identifying of a subject.

Furthermore, the two sides of the database communicate through the API using A-side and B-side keys. This allows data from the B-side to be reassembled into the patient specific data if and when it is necessary. Thus, some embodiments of the present inventive concept address many of the disadvantages discussed in the background related to manipulating, searches, sharing etc. big data as will be discussed further below.

Figure 3:
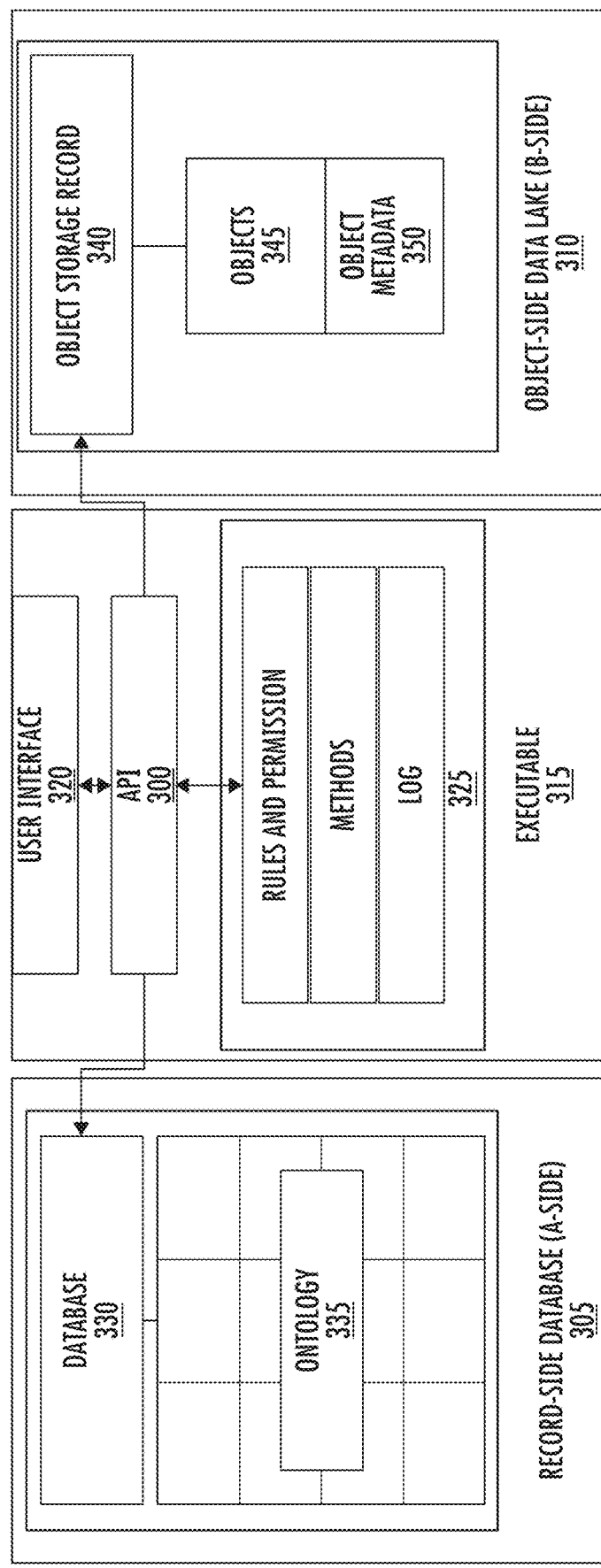
FIG. 3 is a block diagram illustrating an application programming interface (API) having dual databases in accordance with some embodiments of the present inventive concept.

Referring now to FIG. 3, a block diagram illustrating an API in accordance with some embodiments of the present inventive concept will be discussed. As illustrated in FIG. 3, the API 300 operates between the Record-side Database 305 (A-side) and the object-side data lake 310 (B-side) as discussed above. In some embodiments the API 300 may be included with an imaging system itself (resident on the imaging device), however, it may also sit between devices without departing from the scope of the present inventive concept. The executable 315 portion of the API 300 may include its own user interface 320 and its own directory manager 325 including rules and permissions, methods (processes), log etc. Once the image is obtained and is received by the API, the image is stored by reference in the Database 330 (A-side) and the image itself is stored as an object in the Object-Side Data Lake 310.

All metadata associated with the acquisition of the image and the image itself is stored according to a data model appropriate to the use case. This data model constructed in the context of an ontology 335 for a specific Exam that may include all or a subset of the ontology described in FIG. 1. Herein, the broad data model for the acquisition and management of images and data in the context of medical applications is referred to as the Translational Imaging Innovations (TII) Data Genome. Each unique body of information forms a subset, or Gene, of the TII Data Genome. For example, each specific imaging system has a unique set of defining characteristics, and these characteristics are the Gene for the imaging. The ontology defines the scope of the data that may be managed and stored in the database and defines the scope of operations that are programmable from the API. The Genes provide low-level specific data models that may be "discovered" or added to the data model and database over time without perturbing the structure of the data model.

Providing the database 330 in the Record-Side Database 305 removes the need for a developer to create a database of his/her own for each individual system. As further illustrated in FIG. 3, the object-side data lake 310 includes the anonymized object storage records including objects 345 and object metadata 350. The A-side and B-side databases can only access one another using unique keys associated therewith. Anonymization of data on the B-side simplifies development of a hardware system and essentially creates a "plug in" for the imaging device. A "plug in" generally refers to a software component that adds a specific feature to an existing computer program by essentially plugging in.

Users can create custom queries for the data stores using, for example, the user interface 320. The user interface 320 can take any form known to those of skill in the art, for example, a keyboard, mouse, touch screen, voice command etc. The query structure in some embodiments may resemble a shopping list/cart. In other words, a user can choose from a list of items that identify what the user is looking for. For example, the list may include subject—what was imaged; what conditions was the subject imaged under; what records are available and the like. Each category has subcategories that can be checked and unchecked as the queries are refined.

Furthermore, the data may be stored in such a way that allows a user to reorganize the hierarchy of the queried data. In other words, a user can look at a folder structure with any hierarchy desired. Modules may be, for example, dragged and dropped or clicked, to indicate order. An example folder tree builder is diagrammed in the Export Collection 400 window of FIG. 4. A list of Available Identifiers 401 defines available folders for data organization. The Folder Tree Builder 402 is a visual hierarchy of the structure given the ordering of the folders 401. A user may add or delete levels according to the identifiers available in the user interface (UI).

A common hierarchy for a multi-study data record may include, for example, Study, Subject, Modality (e.g. imaging modality) and Date Range. A four level folder hierarchy might be as follows: Study/Subject/Date Range/Modality/ {file objects}, but there are 24 ways to order this set of four attributes. Furthermore, it may be organized with only three levels or two levels depending on the user's needs. The construct of the current inventive concept allows the user to visualize data organization in folder structures that they are comfortable with, or that most closely resemble the way they are approaching the data for a specific task. This presentation structure is only a user interface, and does not actually move data internally, and therefore increases the flexibility of data organization without the need for copying data into new organizational constructs, or over thinking the folder structure to begin with.

Some embodiments of the present inventive concept provide for custom naming using tags from structure to maximize efficiency. For example, files may be named in accordance with user preference while maintaining an original name in the code not visible to the user. Thus, files can be recreated when necessary and can be put back in the original format with the original data. In other words, names are applied as a "label" on top of each file, but the original file is always there and is not altered.

Figure 4:
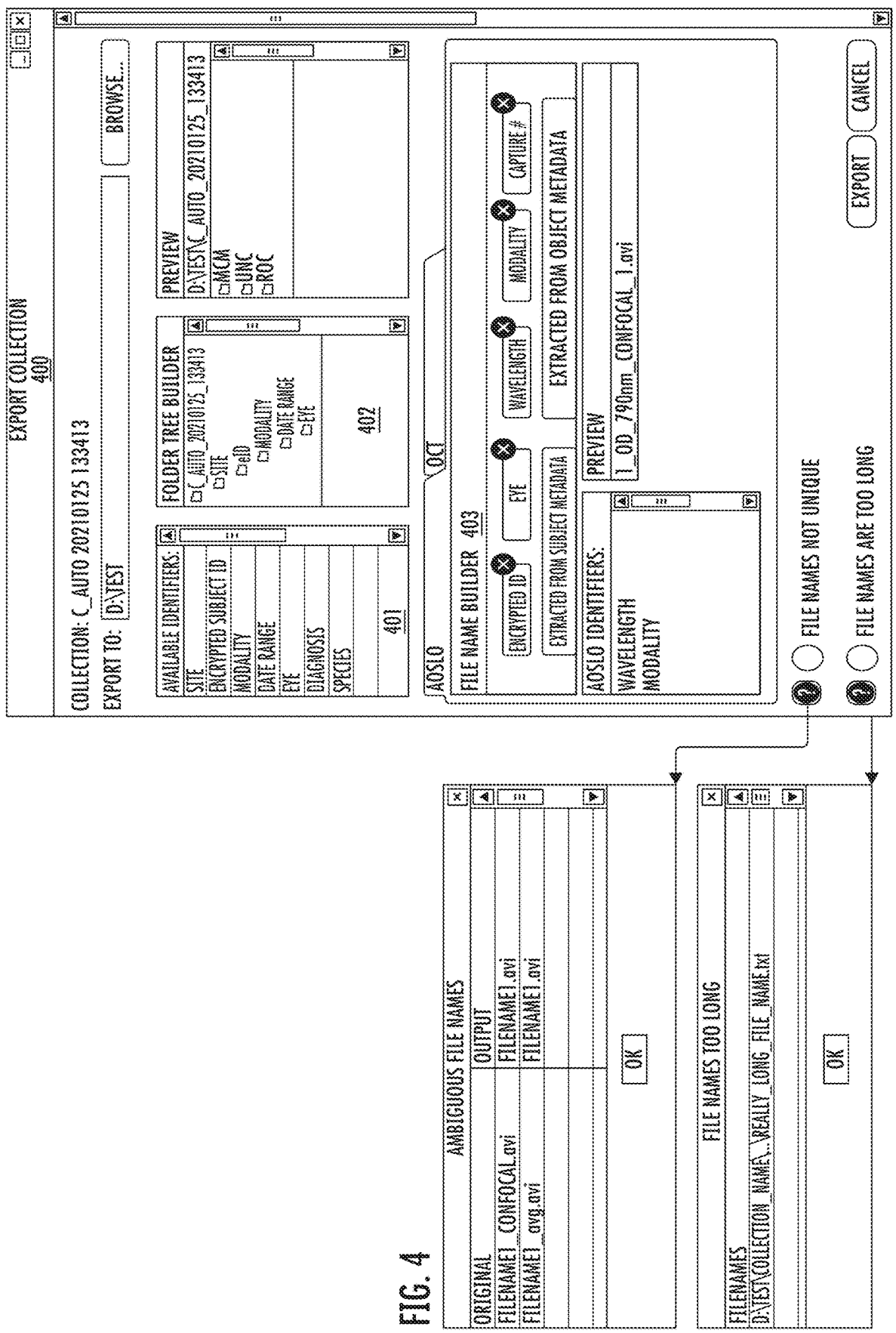
FIG. 4 is a diagram of a user interface and template for file mining in accordance with some embodiments of the present inventive concept.

As shown in FIG. 4, a user may invoke a file name builder 403 on a graphical user interface and draw components of a file name from attributes drawn from the subject metadata and attributes drawn from the object (file) metadata. The file naming method may include error-identification methods, such as identifying names that are not unique or names that are too long for the operating system. A key advantage provided by embodiments of the present inventive concept is that informative file naming is allowed without transcription errors. Furthermore, as a file name is only a label, this construct allows for renaming files for specific use cases non-destructively. As shown in FIG. 4 (403), the file name is an ordered concatenation of encrypted subject ID, eye under test, wavelength of imaging system, image modality, and acquisition sequence number. This is quite useful for operating with image files where one wants to understand the contents at a glance. In other embodiments, the files may be delivered blind to data analysts who must remain unbiased. In such a case, the files may be renamed with an arbitrary code or Universally Unique Identifier (UUID), while being fully traceable to the source through the database given appropriate authorizations.

Figure 5:
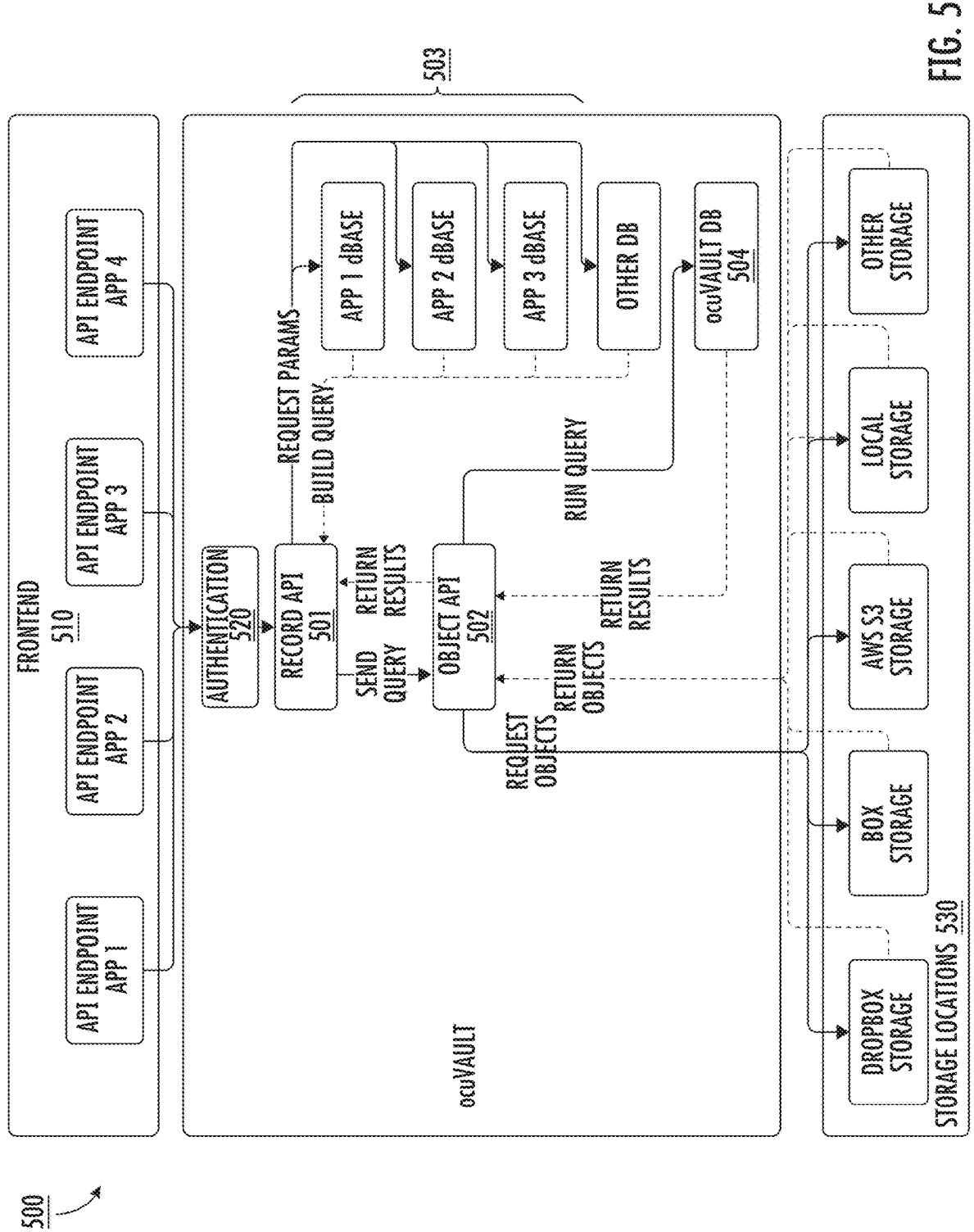
FIG. 5 is a diagram illustrating the architecture and information flows of an API having multiple databases, front ends, storage locations, and authentication in accordance with some embodiments of the present inventive concept.

Referring now to FIG. 5, a block diagram illustrating an architecture for the implementation of the API of FIG. 3 across multiple Record-side databases, object storage locations, and API front ends will be discussed. It will be understood that FIG. 5 is provided for example only and embodiments of the present inventive concept are not limited thereto. Embodiments illustrated in FIG. 5 illustrate how the API in accordance with embodiments herein may be able to manage a multi-client, multi-cloud (storage locations) environment with a common API and common object-side database (Referred to herein as OcuVault DB). The core of the API 500 controls methods that interact with structured records 501 and one or more databases 502, reading and writing records to the main API database 503.

The application layer 510 for the API interacts with the API through one or more endpoints (API endpoint App 1 . . . API endpoint App_n). Between the application layer 510 and the API body 501 resides a validation layer 520. Objects may be stored in any location 530 accessible to the API, including local to the API, in a generic cloud infrastructure such as Amazon Web Services, in a commercial storage structure such as Box or Dropbox and the like. File naming and folder organization problems are removed from the user and controlled by the API, using file naming and folder organization utilities, for example, discussed above, to facilitate visualization and access to data.

Storage Locations 530 in FIG. 5 of the present inventive concept suggest remote, networked, or cloud data architectures. However, in some embodiments, the API may also be resident on a data acquisition device, automate the service of building a database of data acquisition sessions, and automate the secure storage of objects directly onto a storage unit in communication with the acquisition device.

Figure 6:
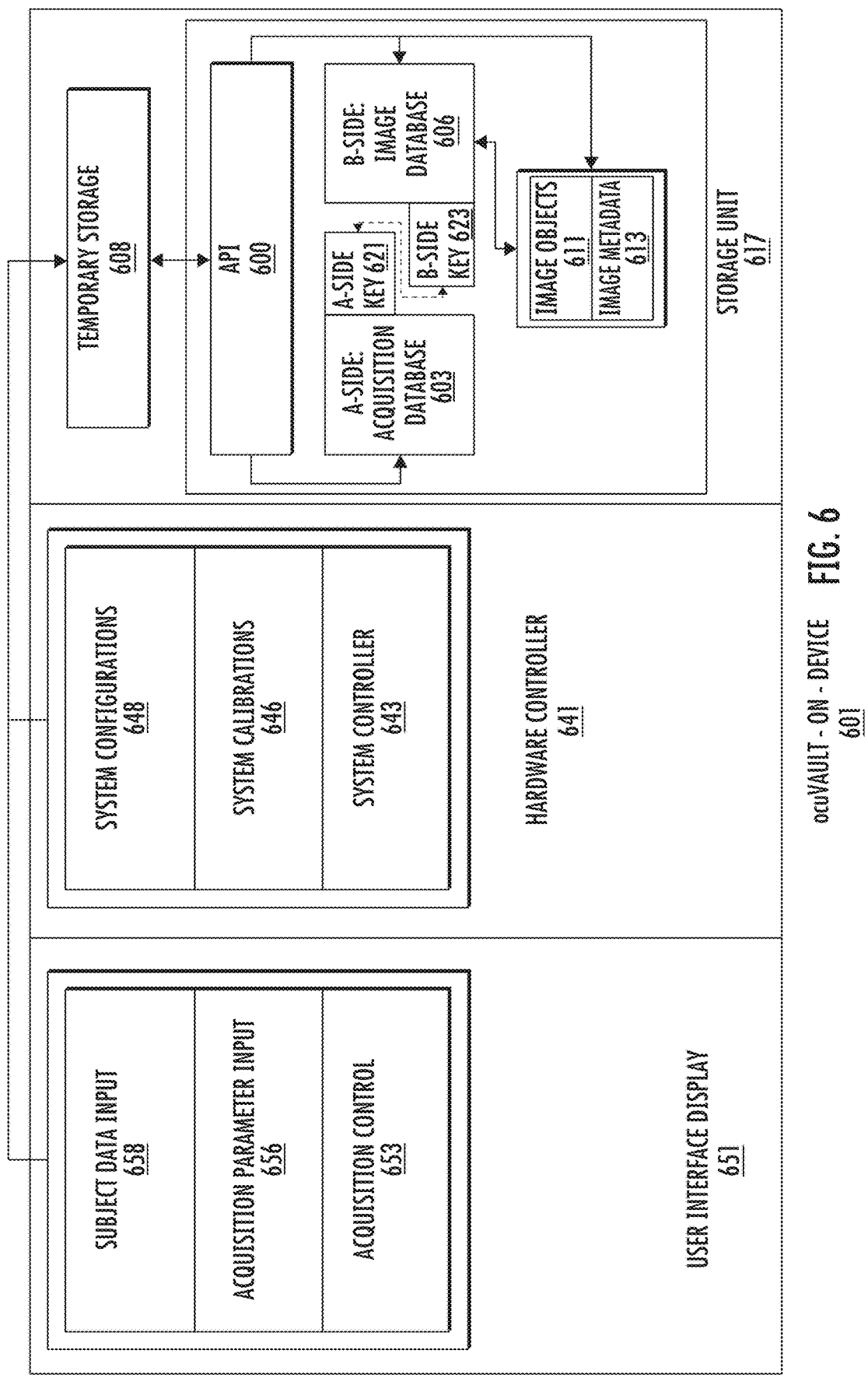
FIG. 6 is a block diagram illustrating an API having dual databases accessed by keys in accordance with some embodiments of the present inventive concept integrated in a storage unit of a device.

Referring now to FIG. 6, a block diagram illustrating an API 600 implemented to manage records and objects specific to an imaging or Exam device having dual databases accessible by A-side 621 and B-side 623 keys in accordance with some embodiments of the present inventive concept will be discussed. As discussed above, the API 600 does not have to sit on the device, it can sit between devices as a bridge without departing from the scope of the present inventive concept. Furthermore, various parts of the system illustrated in FIG. 6 can be at different locations and still have a similar functionality without departing from the scope of the present inventive concept.

As illustrated in FIG. 6, the API (referred to herein as OcuVault-on-Device 601) includes a storage until 617, a hardware controller 641 and as user interface display 651. Although the hardware controller 641 is shown as including system configurations 643, system calibrations 646 and a system controller 648 and the user interface display is shown as including a subject data input 658, an acquisition parameter input 656 and an acquisition control 652, embodiments of the present inventive concept are not limited thereto. More modules may be added and/or removed without departing from the scope of the present inventive concept.

In the configuration shown in FIG. 6, ocuVault-on-Device 601 mediates a data management contract between an acquisition system and data storage. The contract may specify what data from the acquisition system 603 is to be temporarily stored (temporary storage 608) and where, signal the API that an acquisition sequence is complete, and the API may then perform the service of collecting the data, filling the record-side and object-side databases (603 and 606), and stores the data objects, e.g., image objects 611 and image metadata 613. In some embodiments of the present inventive concept, all PHI/PII shall stay resident in in the record-side database (A-side 603). The object side database (B-side 606) shall include a reference to the storage path of the object and a set of defining attributes, agreed in the contract, for querying the object-side database (B-side 606). The record-side database (A-side 603) shall be linked to the object-side database 606 through an exam (time-point-of-acquisition) key. Furthermore, all metadata associated with object necessary to read and analyze the object shall be recorded in a java script object notation (JSON) or similar record associated directly with the object. In some embodiments of the inventive concept, the object shall be stored in one of two formats: either a proprietary format explicitly defined by the customer, or a digital imaging and communications (DICOM)-conformant format. Metadata associated with object includes configuration and calibration information associated with the acquisition of the object. Metadata associated with the object includes all DICOM-conformant tags provided by the customer in the contract.

In some embodiments, ocuVault-on-Device 601 is installed as a Restful API on an examination device. A RESTful API refers to API or web API that conforms to the constraints of REST architectural style and allows for interaction with RESTful web services. A data model for examination is pre-defined as a subset of a master data model, and the data model has a mapping to a relational database managed by the API.

At the conclusion of an examination, or a single data acquisition of a patient or subject with the device, the device software writes any examination metadata and observational records to a tagged file that is consistent with the data model and saves the file to a predetermined location. The tagged file may be a JSON file, and XML file, a CSV file, or the like without departing from the scope of the present inventive concept.

The data files include any or all the structured records that are associated with the examination, available from the device, and consistent with the data model. These records may include patient metadata, examination metadata, and notes. These records may be available on the device because they have been, for example, downloaded through an external records system, such as an EHR system, read in via a barcode, or input through a graphical user interface (GUI).

The structured record may also include any or all of the device configuration settings that determine the device operation, computations, displays, or any other behaviors that support the record of the examination.

The structured record may also include information specific to accessories used during the preparation or conduct of the examination. Such accessories, without limitation, may be, for example, a specific objective lens used during imaging, a record of an intervention, such as pupil dilation, applied prior to or during the examination and the like.

The record may further include information on critical subsystems of the device. For an optical imaging system, subsystems may include, for example, light sources, detectors, spectrometers and the like. Information related to such subsystems may include, for example, serial numbers, calibration data, firmware versions that may provide information on the history of the subsystem that supports quantitation analysis that depends on the subsystem and/or related to the quality record of the subsystem.

The structured record is defined a priori for the device, and the system software only needs to populate data into a linear file with a known set of tags for each record at the conclusion of each acquisition.

Figure 7:
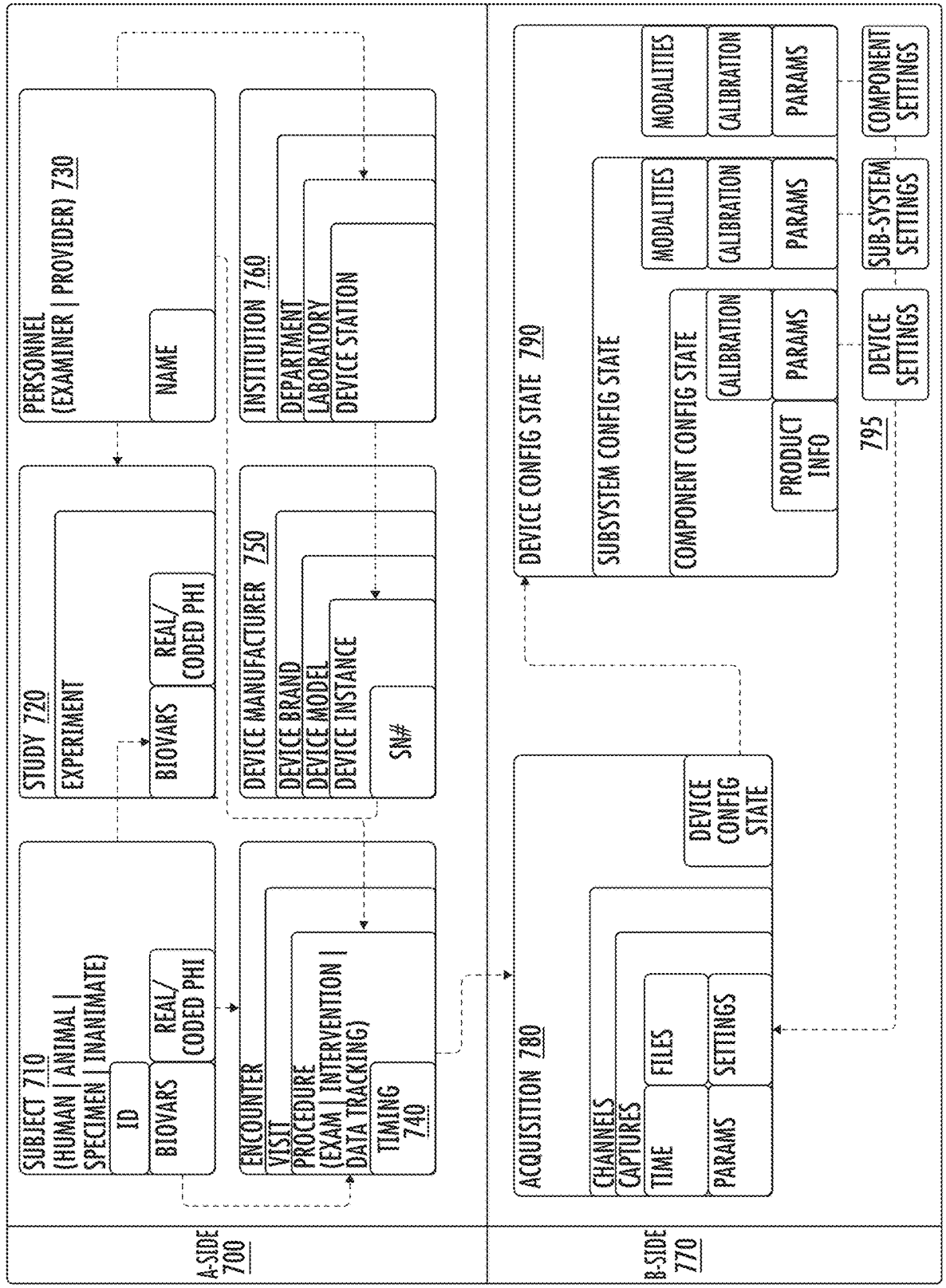
FIG. 7 is a block diagram illustrating a data model, or Gene, for an exam in accordance with some embodiments of the present inventive concept.

Referring now to FIG. 7, an example data model or Gene that may be used for an exam in the context of the present inventive concept will be discussed. As illustrated, the data model includes the A-side 700 and B-side 770 construct discussed above with respect to the system. As further illustrated, the A-Side data 700 include structures for Subject 710, Study 720, and Personnel 730. As used herein, Personnel refers to, for example, physicians and staff that conduct an examination. The A-side data also includes records pertaining to the Encounter 740, the device or instrument used in an exam 750, and the location of the exam 760.

In the data model illustrated in FIG. 7, the B-side construct 770 includes information pertaining to the data acquisition, including parameters that define the acquisition 780, parameters that define the state of the device at time of acquisition 790, and specific device and subsystem settings at the time of acquisition 795.

In addition, the device saves any objects associated with the exam, independently of, but along with the structured record file. Such objects may include, for example, formatted reports, spreadsheets, image files, configuration files, or other types of information without restriction. The file types may be, for example, portable document format (PDF) files, Microsoft Word files, tag image file format (TIFF) files, joint photographic experts group (JPEG) files, portable network (PNG) files, DICOM files, and the like without departing from the scope of the present inventive concept. Furthermore, the device may save source data, and the source data may be one or more data files that are derived from the source, and the source filed may be raw files that are unprocessed, subjected to specific pre-preprocessing steps, or may be processed to final state as determined by the device manufacturer for the intended use.

For example, a digital camera my output a color image into a digital negative (DNG) file or a JPG file. The DNG file is "source data" for subsequent processing and enhancement in a digital darkroom, such as Adobe Lightroom or Capture One. But the DNG file has already been processed from sensor pixel data using proprietary color science algorithms of the camera vendor. The color science algorithms provide the interpolation and smoothing required of a sensor that is covered by a specific color filter, such as a Bayer filter (U.S. Pat. No. 3,971,065) or a Fujifilm X-Trans sensor (U.S. Pat. No. 8,531,563) to produce a pleasing full color response.

In embodiments using color digital cameras, it may be desirable to save the pixel intensity values directly from the sensor prior to application of the color science algorithms, in addition to or instead of, the processed DNG (Adobe digital negative format).

The associated data model for a digital camera my include definition of the color filter array disposed over the sensor and may further include a calibration function that maps spectral efficiency function to specific pixel values. The data model may also include a distortion map associated with the sensor array alone or in combination with a lens used to acquire an image.

Imaging processing pipelines for monochrome or color digital sensors are discussed, for example, in U.S. Pat. No. 8,330,772 entitled IMAGE SIGNAL PROCESSOR FRONT-END IMAGE DATA PROCESSING SYSTEM AND METHOD. U.S. Pat. No. 8,743,229 entitled IMAGE PROCESSING METHOD AND APPARATUS FOR BAYER IMAGES describes a set of processing steps to produce an image from a sensor that includes a Bayer filter. U.S. Pat. No. 5,606,365 entitled INTERACTIVE CAMERA FOR NETWORK PROCESSING OF CAPTURED IMAGES discusses processing or correcting a color image with information downloadable from a database. Unique to the present inventive concept, the source data at the pixel level accompanies a set of metadata, calibration information, and error correction information in an electronic binder, or traveler that flows with the recorded object from the time of acquisition. Such low-level data may originate with the camera manufacturer or may have been updated through by the manufacturer, camera owner, or other third-party. This data need not be open sourced to every user. Encryption and password protection may be applied to limit access without deviating from the objective of the inventive concept to provide immediate access to authorized user of low-level data for maintaining provenance of data or enhancing postprocessing and analysis of source data.

Another example of providing a precursor image can be found in the field of Fourier Domain Optical Coherence Tomography (FDOCT). The depth-dependent spatial cross-sectional image is formed from the Fourier Transformation of a wavelength-dependent interferogram, following a sequence of pre-processing steps, as discussed for example, in U.S. Pat. No. 8,401,257 entitled METHODS, SYSTEMS AND COMPUTER PROGRAM PRODUCTS FOR PROCESSING IMAGES GENERATED USING FOURIER DOMAIN OPTICAL COHERENCE TOMOGRAPHY (FDOCT). The clinically relevant image object is the spatial domain image. The process of Fourier transformation destroys phase information that is present in the original spectral domain, for example, wavelength dependent data.

It is often valuable to preserve the spectral domain data. To be useful, the spectral domain data requires certain calibration information that is used to complete the Fourier transformation. This calibration information includes the mapping of the correct wavelengths to the spectral domain pixel values, and may further include dispersion compensation parameters that correct for the optical system of the device or the subject under test, or both.

In some embodiments of the present inventive concept, the spectral domain data is preserved as an object of the examination, and the spectral calibration and dispersion coefficients for the device and the subject under test are preserved in the structured metadata file.

In some embodiments of the present inventive concept only the spectral domain object and necessary calibration coefficients are stored; the Fourier-transformed spatial domain image is not stored immediately, and rather can be recreated at a later stage with spectral domain object and the associated metadata.

A particular value of preserving such image data in the spectral domain is in securing PHI from unauthorized access. FDOCT is commonly used in retinal imaging, and an image of the retina is PII and PHI. The spectral domain precursor is not PII or PHI, and requires processing with the associated metadata, or calibration and compensation factors to recover an image. This metadata may be protected through encryption in the metadata file, such that only authorized recipients can complete the processing steps to generate the spatial domain image. While this method does not offer foolproof security, it will be understood that sufficient a priori knowledge exists to constrain a search for a set of processing parameters that recovers the target spatial domain image, it does prevent incidental disclosure of PHI, while preserving information that may be useful in recovering phase information, phase variation over time that may accompany blood flow, and in assessing spectroscopic information associated with the patient or subject under test.

Figure 8:
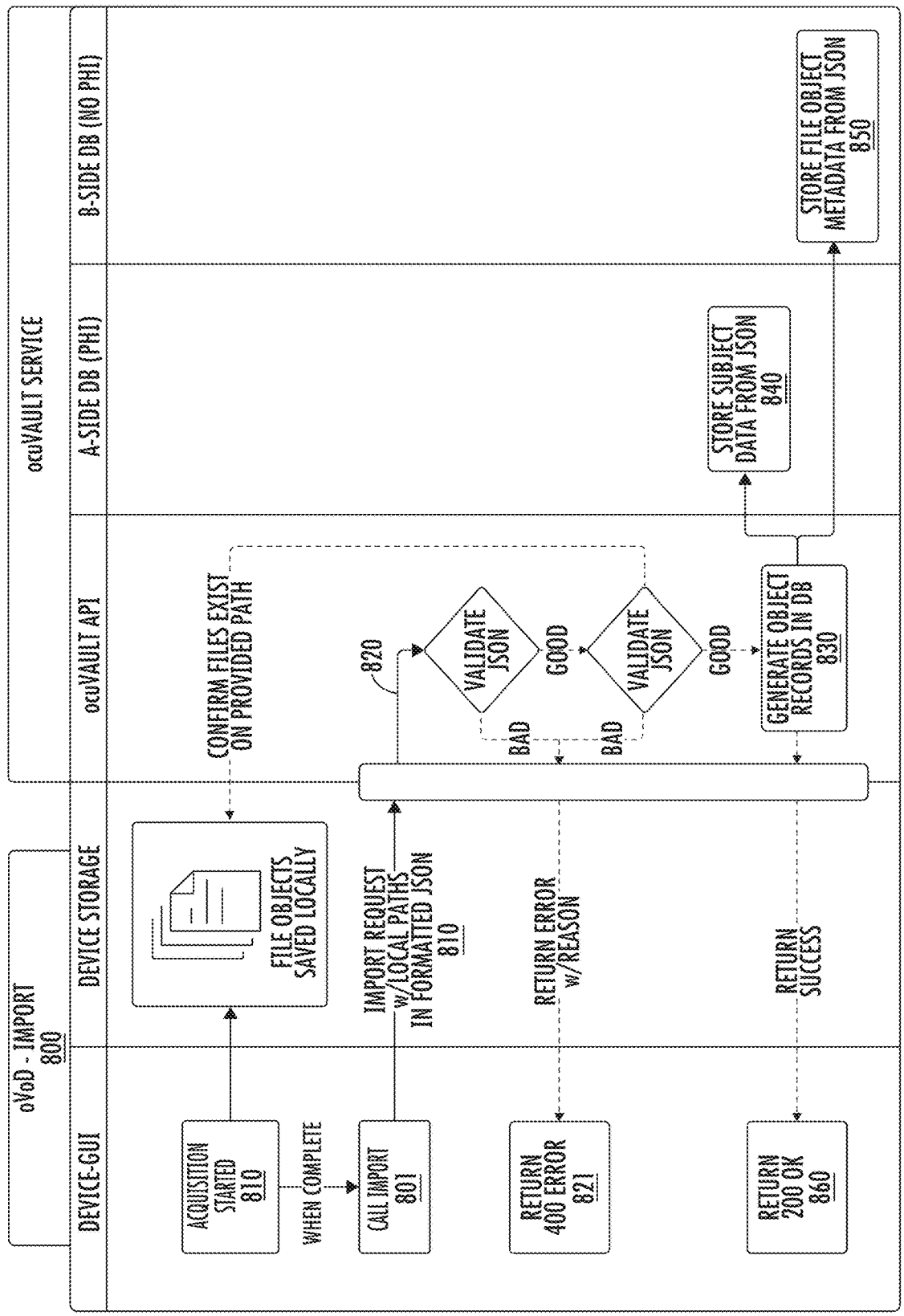
FIG. 8 is a block diagram illustrating import functionality of an API in accordance with some embodiments of the present inventive concept.

Referring now to FIG. 8, a flow diagram illustrating the import functionality of the API in accordance with embodiments of the present inventive concept will be discussed. As illustrated, after an acquisition 810 is completed, the API import 801 is initiated, a set of structured records is written to a tagged file (e.g. JSON) and a set of file objects is saved with the JSON file a target location 810. The API validates 820 the JSON record and then validates the files referenced by the JSON record. Errors, if any, are written to a log file 821.

The structured file is read by the computer code, and the tagged records are recorded to a relational or hybrid database accessible to the API 830, where the database schema is precast as the blueprint, or genome for the data model, including not only the sets of tables and fields to hold the data, but includes the common relational structures as well for recording relationships of studies, patients, encounters, and examinations that form the context of the broader model.

The API code stores the tagged file 840 or a copy thereof into a secure storage location, referred to as the A-Side storage discussed above. As discussed, A-side storage may retain PHI as a source record.

The API creates a second copy of the tagged file, stripped of all PHI, and stores this copy 850 to B-Side storage as discussed above. The tags themselves, by design of the API and data model, define PHI vs non-PHI information, and therefore no additional algorithm intelligence is required to parse the tagged file into the A-side and B-side counterparts.

The API stores the path to the object files, either according to their original location or after a copy or move action according to system preferences, in the database.

The API performs a validation that the operations were successfully completed. This validation may include, for example, confirmation that the tagged fields are appropriately formatted, and that object files are in their correct location.

The API sends a message 860 to the device that the operations were completed, provides a log of actions undertaken, and a log of error messages for the case that validation failed 821 (Return 400 Error). The API returns to its RESTFul state pending the next examination or acquisition.

In some embodiments of the present inventive concept, the system software of the device may invoke the API, the API may read for data in the target storage location, or the API may be invoked periodically using a scheduler. Other triggers for invoking the API may be appropriate to a particular use case, without deviating from the intent of the inventive concept.

In addition to these data ingestion methods of the API, the API may include other methods useful to the transfer and utilization of the records, objects, and database managed by the API. For example, the API may automatically create a structured file object by combining structured records stored in the tagged file with one or more of the unstructured file or image objects. A digital camera image file may be converted to a DNG file by combining the image object with tagged metadata into an exchangeable image file (EXIF)-equivalent data structure. A medical image may file may be converted into a DICOM file by converting the source object into the DICOM image format and mapping the tagged metadata record to DICOM tags.

A distinct advantage provided by the present inventive concept over the conventional systems and methods is the extensibility of the conversion methods to source objects not originally envisioned by conventional approaches. For example, in accordance with embodiments of the present inventive concept, a DNG file may be created by invoking the API to create a two-dimensional (2D) cross section from a volumetric Optical Coherence Tomography (OCT) image and publishing this extracted 2D image to a DNG-conformant file.

Another distinct advantage of the present inventive concept over the conventional systems and methods is the automation of publishing source data to DICOM conformant files, even where a specific DICOM standard or supplement does not yet exist. In such a circumstance, any data that may be rendered as one or more frames of an image may be converted into DICOM-readable format, either as direct representation of the source data or after a post-processing step. The data model of the present inventive concept is expressly mapped to DICOM tags as follows. DICOM reserves even-numbered tags as public tags and odd-numbered tags as private tags. Among the even numbered public tags, some are defined as mandatory (to claim DICOM conformance) and some are optional.

Operations of the API according to some embodiments of the present inventive concept include populating DICOM tags with the API metadata tags according to the following rules: [1] Populate mandatory public tags with available metadata; [2] Populate optional public tags with available metadata; and [3] Populate private tags using proprietary metadata drawn from the data model of the present inventive concept into a private, but common, set of DICOM tags reserved for the API (as allowed by the DICOM standard), as listed, for example, in the table of FIG. 9. It will be understood that the Table in FIG. 9 is provided as an example only and embodiments of the present inventive concept are not limited thereto.

A further advantage over conventional systems and methods is the automation of publication of a DICOM readable file independent of the source if whatever metadata that is made available is written into a tagged file according to the present inventive concept. The API handles public versus private information and handles PHI versus non-PHI information. A simple set of preferences guides the DICOM publication process, for example, "include (or exclude) PHI," "include (or exclude) private information," "Encrypt PHI," and similar preferences.

Furthermore, a DICOM file is automatically tied to a relational database, and the relational database at its source is common to every other relational database in a common family built and according to the present inventive concept. Thus, while define and implement a data model for the management of medical, and specifically ophthalmic images, many other data models that are similar in detail or a level of abstraction may be envisioned and created that offer the benefits of the present data model and its associated API, without deviating from the intent of the inventive concept.

In some embodiments of the present inventive concept, the API may be used to publish a secure, traceable, and tamper-resistant data object for the transfer of examination data to an authorized receiver. In the field of clinical trials, for example, source document control is required. It is essential to ensure the provenance of data, trace data to its source, and ensure that such data has not been modified on its journey.

Figure 10:
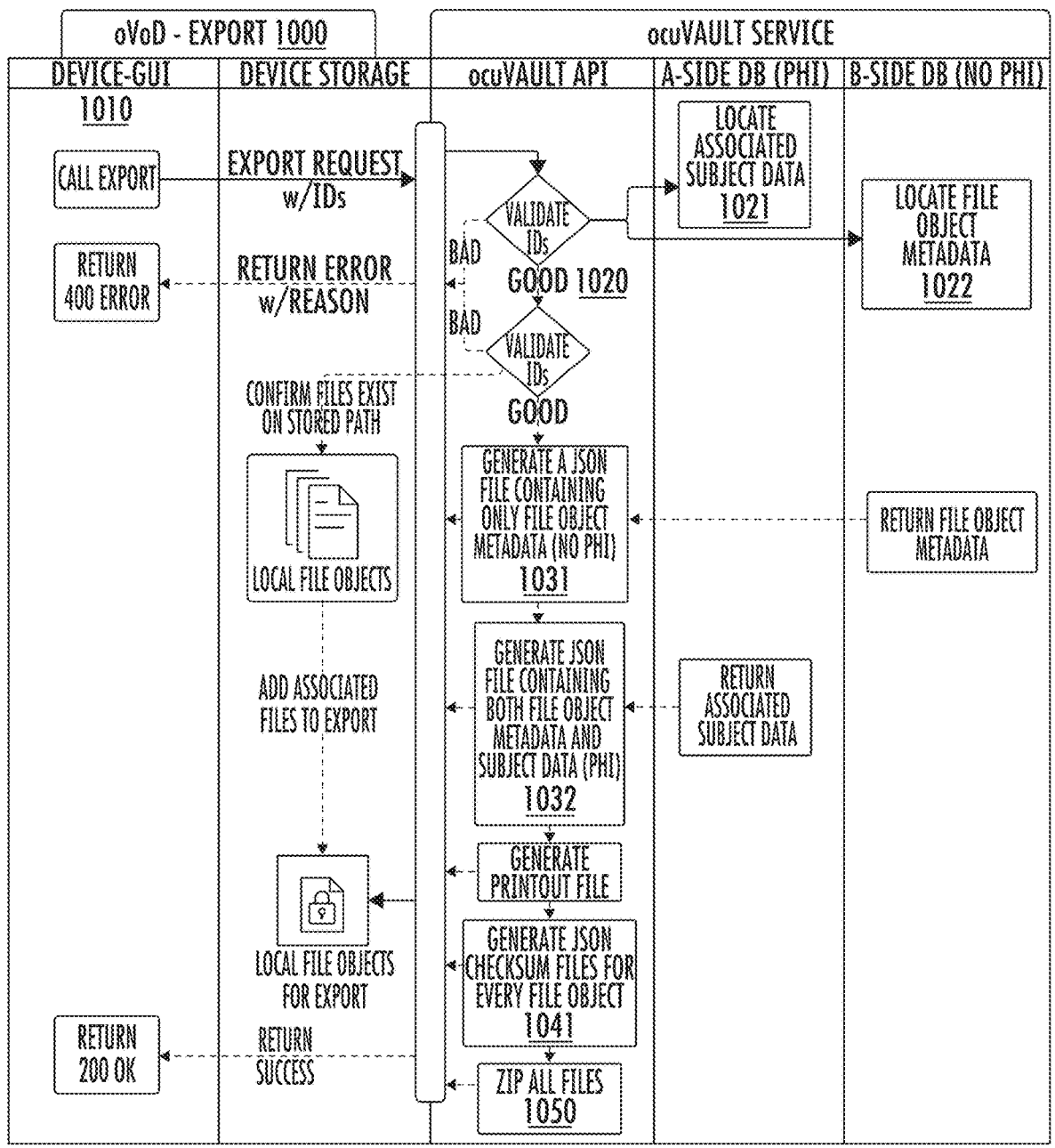
FIG. 10 is a block diagram illustrating an API including a method to publish, or export, a digital binder that contains a multiplicity of elements in accordance with some embodiments of the present inventive concept.

In some embodiments of the present inventive concept, the API 1000 may publish, or export, a digital binder that contains a multiplicity of elements, as illustrated in, for example, the flow diagram of FIG. 10. The elements may include a first tagged file of metadata associated with the examination. This tagged file may be the A-Side filed discussed above, or a subset, and may include PHI, coded information tied to PHI, or may be free of PHI. The binder may include a second tagged file of metadata associated with the examination. This tagged file may be the B-Side file discussed above, or a subset, and will be free of PHI. The binder will additionally include any source objects that are useful to the processing and analysis of the examination record. These source objects may be the source image file and may additionally include configuration files or any other files generated during the examination that are captured and managed by the API. The record of each such stored object includes a universally unique identifier (UUID) stored in the database, and this are traceable objects.

Referring now to FIG. 10, the export process by the user or system invoking the API to initiate an export 1010 with required set data IDs as may be identified from the device user interface or a query to the API database. The API validates 1020 that the IDs are valid, and that data is available, locating the subject data 1021 from the A-side database and the file object metadata 1022 from the B-side database.

Two JSON (or equivalent) files are generated from the database for the data to be exported: a file containing object metadata only 1031 and a file containing both object and subject metadata 1032 (the latter may exclude or code PHI).

A checksum 1041 is created for each such object using technologies known in the art, such as the SHA256 Hash Generator, and the resultant checksum is stored along with object in the binder, i.e. a zip file 1050 or similar. The hash is now identified with the UUID and may also be stored in the database or distributed separately to the authorized data recipient, and thus provides a traceable record for tamper-testing.

The binder with its objects, files, and hash codes may be compressed and may be encrypted into a single electronic binder, for example as a zip file, for transport to an authorized recipient.

Upon receipt, a counterpart to the API can perform automatic validation of the object. The hash codes can be tested to ensure that the independent files have not been corrupted. The tagged files can be read for critical information such as patient/subject under test, exam date, and the like. Any observational records can be read to compare to competing record that may have been transcribed separately into a different electronic data capture (EDC) system.

Further, the data binder contains all (most) information relevant to the source object, such that the binder may be imported automatically into the recipient's database, having been constructed according to the model of the present inventive concept and according to the common data model associated with this use case.

In some embodiments of the present inventive concept, the API may provide publication of PHI-free examination results for analysis, with all information required for analysis in one object or one such binder, drawn from public and private tags as necessary. This embodiment automates deidentification of data so necessary to the processing and analysis of human subject data, and necessary to any blinded analysis whether involving human subjects or not. UUIDs preserve traceability back to the source.

Figure 11:
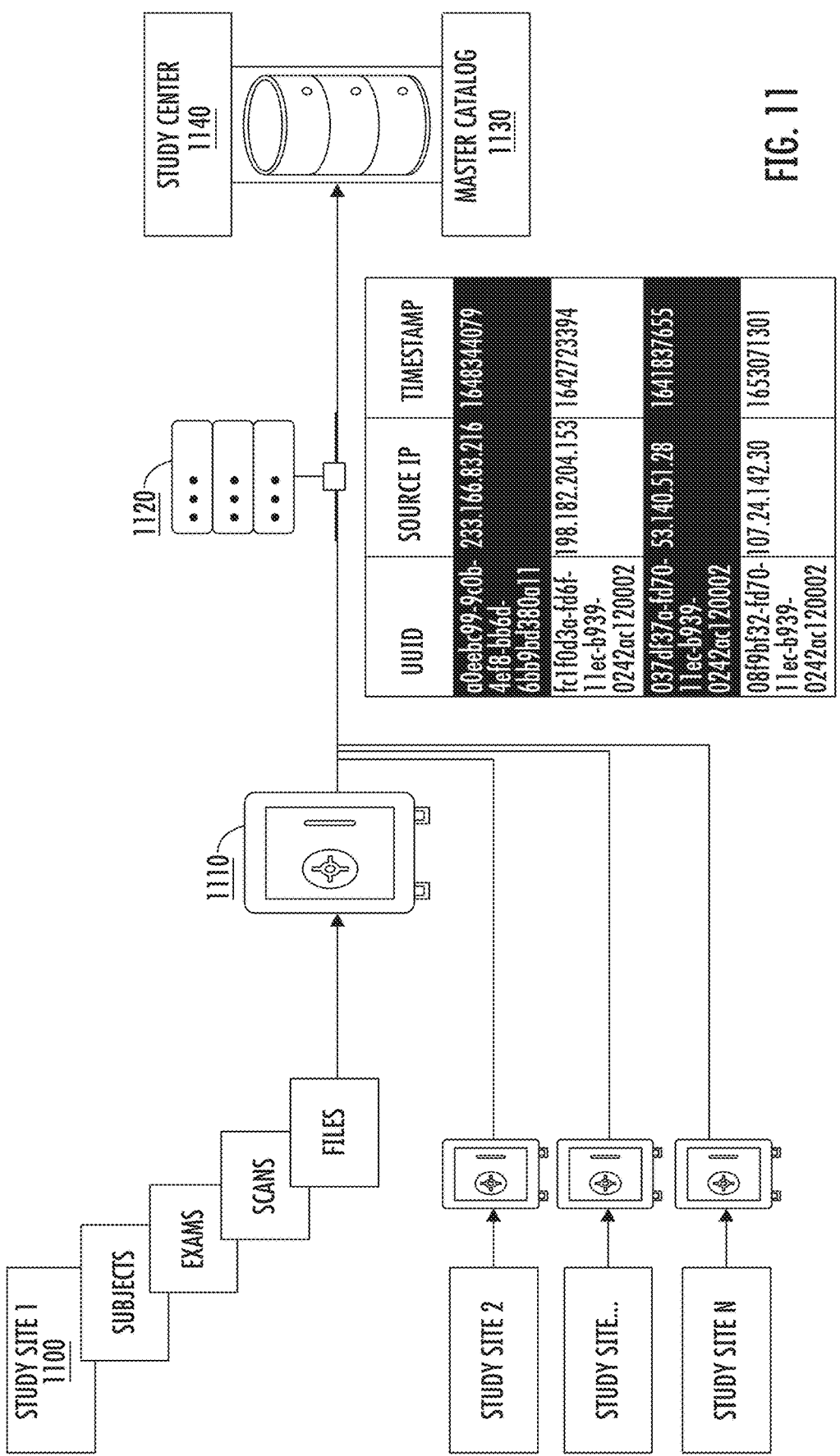
FIG. 11 is a block diagram illustrating a system in accordance with some embodiments of the present inventive concept.

In some embodiments of the present inventive concept, the electronic binders are distributed to the recipient from the source over a network via one or more pre-defined servers, where the record of source, destination, and UUID of the binder (and/or UUID of each independent object in the binder with or without its hash code) is recorded at the server, as illustrated, for example, in FIG. 11.

Referring to FIG. 11, multiple sites 1100 contribute data via their local API export into secure binders 1110 that are transmitted over a network through a dedicated server 1120 that records UUIDs of the binders and internal objects, the source IP address, and a timestamp. Additional information may also be recorded, including the binder size (e.g. in MB or GB), number of objects within the binder, and so on. This transport path provides immediate traceability, and as no information is read from the electronic binder other than UUID, preserves privacy and security. The binders are finally transported to a study coordinating center 1140 for import into a compatible master database, or catalog, 1130.

As is clear from the embodiments discussed above, some aspects of the present inventive concept may be implemented by a data processing system. The data processing system may be included at any module of the system without departing from the scope of the preset inventive concept. Exemplary embodiments of a data processing system 1230 configured in accordance with embodiments of the present inventive concept will be discussed with respect to FIG. 12. The data processing system 1230 may include a user interface 1244, including, for example, input device(s) such as a keyboard or keypad, a display, a speaker and/or microphone, and a memory 1236 that communicate with a processor 1238. The data processing system 1230 may further include I/O data port(s) 1246 that also communicates with the processor 1238. The I/O data ports 1246 can be used to transfer information between the data processing system 1230 and another computer system or a network using, for example, an Internet Protocol (IP) connection. These components may be conventional components such as those used in many conventional data processing systems, which may be configured to operate as described herein.

Various embodiments of the present inventive concept have been discussed. These embodiments are meant as examples only and do not limit the overall inventive concept. Some embodiments of the present inventive concept provide an automated method to receive images and metadata from an acquisition device, parse metadata into data entities based on a standardized ontology, automatically write the data acquisition record into an acquisition side database, format images into a standardized image format, store images onto recording medium, include in the image format a set of information necessary to visualize and quantify the image, populate a storage record into a storage side database, link the records between the acquisition side database and the storage side database with a unique code.

As discussed, in some embodiments, the acquisition side database may include data elements associated with the subject under test and the condition of test, including any personally identifiable information (PII) of the subject under test, where PII includes protected health information (PHI), and where the storage side database excludes all PII.

Figure 13:
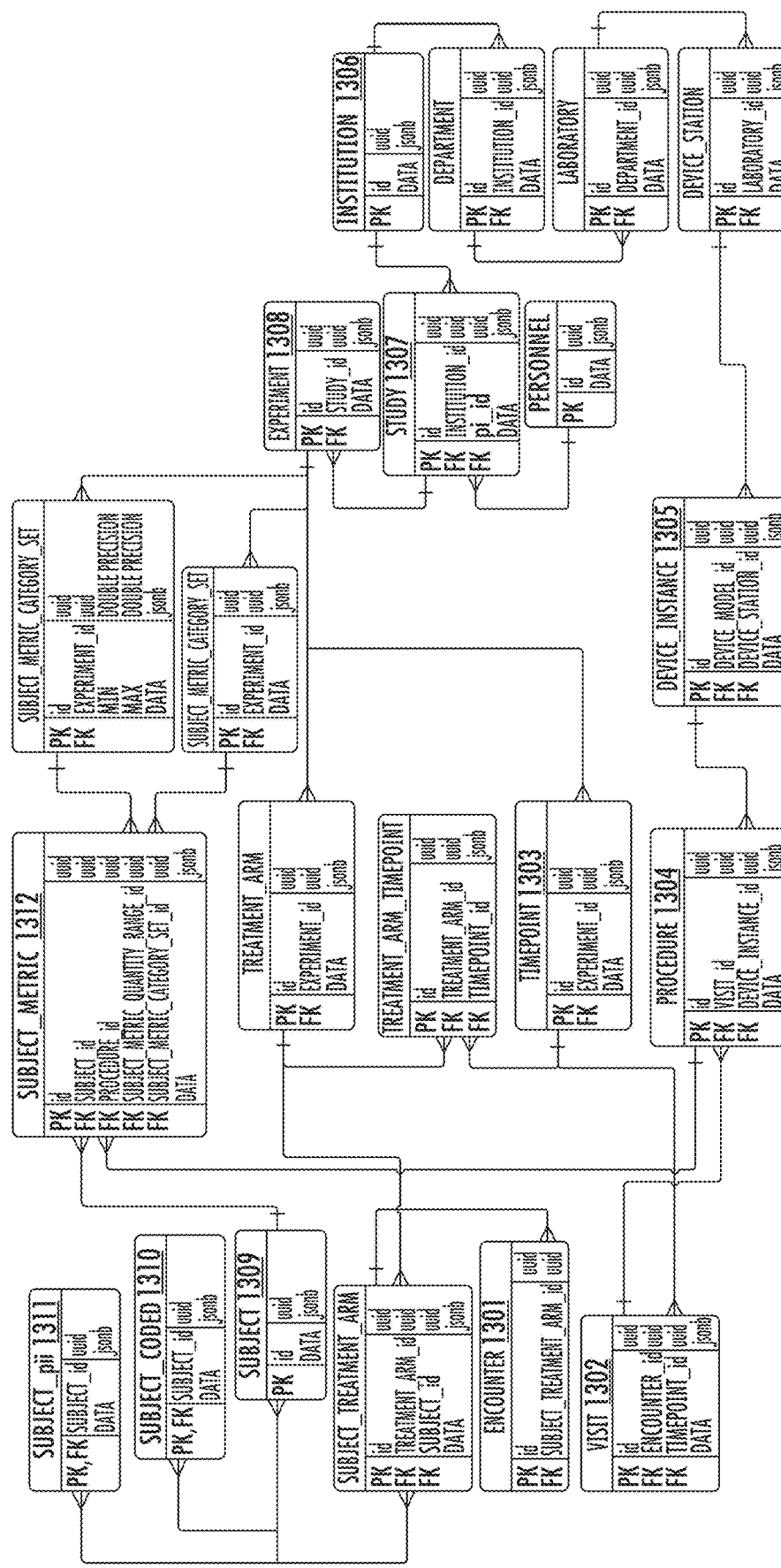
FIG. 13 is a diagram illustrating operations of the A-side database in accordance with some embodiments of the present inventive concept.

Referring now to FIG. 13, a diagram illustrating operations of the A-side database in accordance with some embodiments of the present inventive concept. As illustrated in FIG. 13, the A-side database schema stores sensitive and PII-related data based on uniquely identified subject encounters 1301 with a one-to-many relationship to discrete subject visits 1302 at specified timepoints 1303. When a procedure 1304 is performed during a visit 1302, it is uniquely identified to a specific device instance 1305 by a universally unique identifier (UUID). The device instance 1305 data encapsulates not only information about the device itself, but also its physical location within an institution 1306, the associated study 1307 or studies it is used, and the individual experiments 1308 conducted within each study. Each subject 1309 has data stored under 2 logically separated levels: coded data 1310, and PII data 1311. Therefore, when accessing the database, a service or user is either granted access to subject data through the coded table 1310 where all PII fields are obfuscated, or through the PII data table 1311 where all PII fields are fully accessible. Finally, the group of associated subject, procedure, and data sets for the encounter is uniquely identified and stored in the subject_metric table 1312.

In some embodiments, all information necessary to analyze the image may be stored in a data record directly accessible with the image. The data entities may include the following: definition of the imaging method; definition of the hardware used to acquire the image; definition of configurations and setting used in the image acquisition; and calibration information associated with quantitative interpretation of the image.

Figure 14:
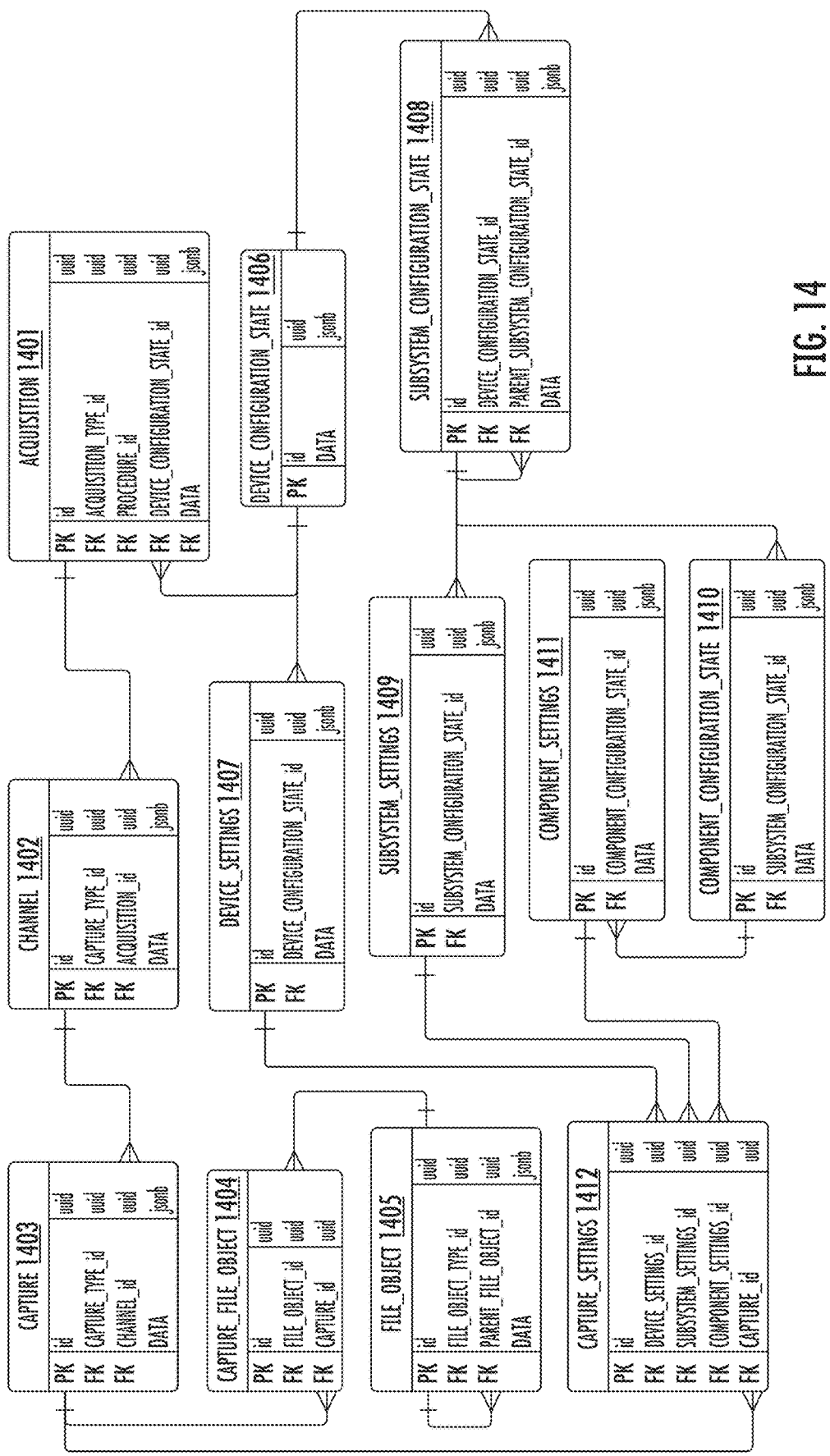
FIG. 14 is a diagram illustrating operations of non-PII acquisition data stored in the B-side database schema in accordance with some embodiments of the present inventive concept.

Referring now to FIG. 14, a non-PII acquisition data stored in the B-side database schema is shown. Each acquisition 1401 is defined by its type, associated procedure, and complete configuration of the device used. Each acquisition is made up of channels 1402, potentially including multiple types and modalities. A channel 1402 is associated one-to-many with captures 1403 of various types and parameters stored in JSONB (binary JSON format) data, which is associated many-to-many with stored file objects 1405 through the capture_file_object table 1404 allowing tracking of deeply-nested relationships among the current, and potentially future, file objects 1405. For the acquisition, the complete state of the device and its configuration is uniquely identified, stored, and referenced by the device_configuration_state table 1406, and its child-tables that store each device setting 1407, subsystem configuration state 1408, subsystem setting 1409, component configuration state 1410, and component setting 1411. These individual device, subsystem, and component settings are then uniquely identified as a group in the capture_settings table 1412, and associated with each capture within the acquisition.

In some embodiments, the ontology of the acquisition side database may include the following entities: a subject under test entity; an anatomy under test entity; a test method entity; an imaging system hardware entity; an imaging system software entity; a study entity; a time and date entity; and an examiner entity.

In some embodiments, the Subject Under Test Entity may be divided into two sub-entities, where the first sub-entity is absent of all PII, and where the second sub-entity includes PII.

In some embodiments, the PII sub-entity may be encrypted and accessible only with enabled permission.

In some embodiments, method may be performed on a system having an integrated directory management system.

In some embodiments, the directory management system may include a visual query interface for filtering entity attributes contained within the acquisition side database ontology and pairing with associated objects recorded in the storage side database.

In some embodiments, the results of the visual query interface are displayed in a multi-level hierarchical format, and where the order of the hierarchy may be set by the user in the visual query interface.

In some embodiments, the visual query interface may display a hierarchical structured view of mutually exclusive sets of selection attributes drawn from the data ontology, where the coarsest set of attributes for a comprehensively exhaustive set of attributes, and where within the visual query interface the user may indicate the hierarchical order for presenting the results.

In some embodiments, the set of attributes displayed below the coarsest level may be drawn from key-value pairs defined within the database ontology.

Some embodiments of the present inventive concept provide an automated method to link image and document objects with database records from a first object storage location housing image and document objects and a second storage location housing a database with records, though an Application Performance Interface (API), where the API automatically populates an object-side database, where the object-side database includes a coded-link between each object and a unique event linked to a subject in the record-side database.

Figure 15:
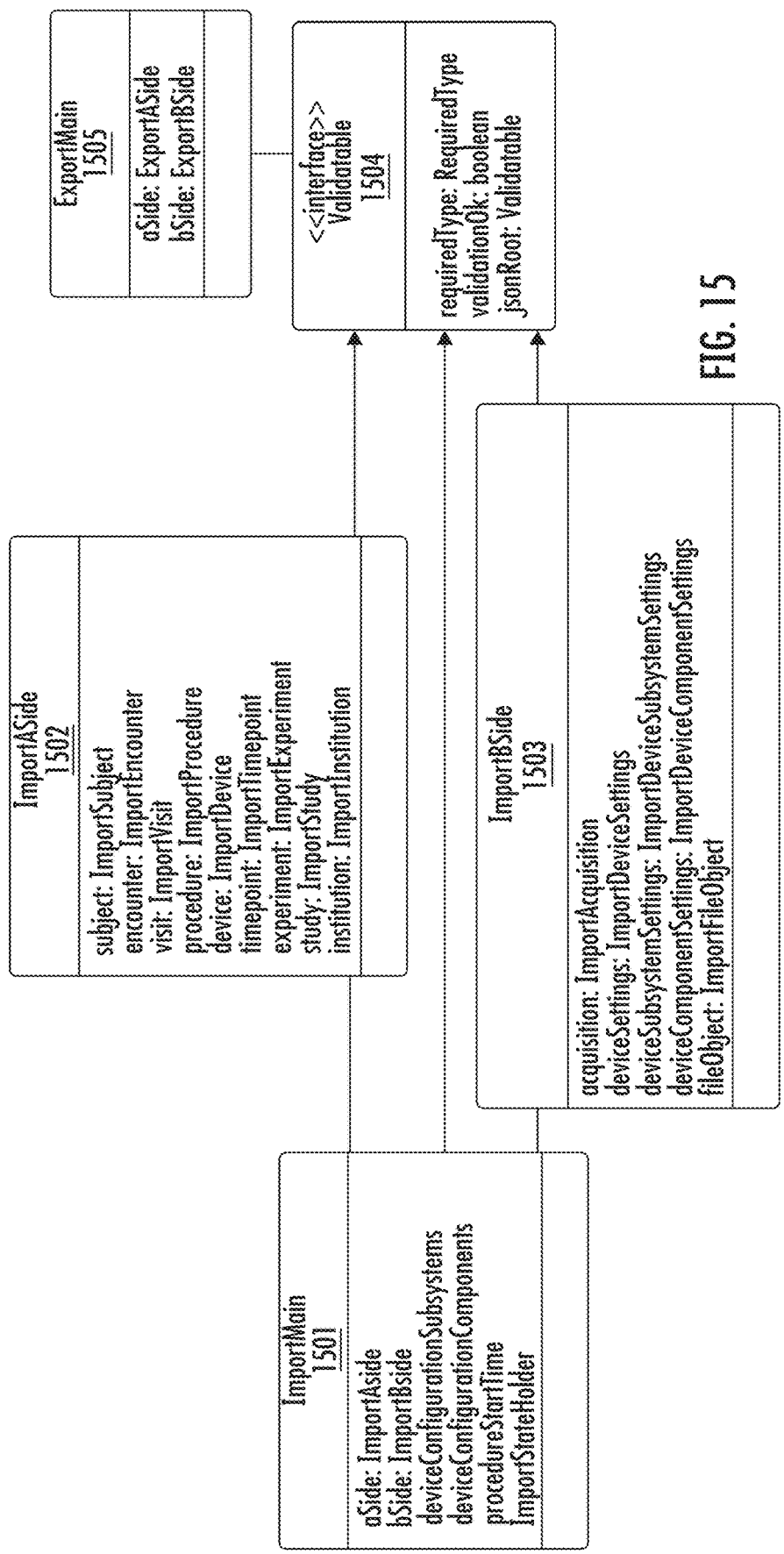
FIG. 15 is a diagram illustrating a data import process performed by the API in accordance with some embodiments of the present inventive concept.

The class structure illustrated in FIG. 15 illustrates the data import process performed by the API. When the ImportMain class 1501 is called, a structured JSON file is specified and the file data is parsed according to its relation to PII, where it's sent to the ImportASide class 1502, or non-PII acquisition data, where it's sent to the ImportBSide class 1503. Upon import 1501, and after the data is parsed by the A and B side classes (1502, 1503), each set of data, A-side and B-side, goes to the Validatable interface 1504 where the data is inspected for valid structure, completeness based on previously defined encounter parameters, known device parameters, dates, file paths, and so on. After validation, universally unique identifiers (UUIDs) are generated each data object within each set of data, A-side and B-side, then standardized and stored internally by ocuVault using the ExportMain class 1505.

In some embodiments, automatically populating an object-side database may include searching a target data lake for objects that match the results of a query initiated from the record-side database, identifying an object in the target data lake, automatically populating a storage path identifier for the object into the object-side database, and returning to the record-side database a key that links a subject record in the record-side database to the object record in the object side database.

In some embodiments, populating an object side database may include populating the database with additional attributes descriptive of the object drawn from the object, including a method type that defines the creation of the object, a hardware definition that defines equipment used to generate the object, a configuration set that defines the operating conditions at use in the creation of the object, a calibration set that provides for quantitative interpretation of the object, as well as including one or more of a file type, a file size, a file creation date and time stamp.

In some embodiments, populating an record-side database may include populating the database with additional attributes descriptive of the object that are drawn from the record, including one or more of an activity type that defines the event creating the object, an anatomy or component of the subject that is the subject of the object, a gender of the subject, an age of the subject at the time of the object curation, and a pathological diagnosis or condition of the subject at the time of object creation, a method type that defines the creation of the object.

In some embodiments, the process of linking the object to the database record may be preceded by one or more actions invoked by the API to modify an object.

In some embodiments, the modification of the object may include encrypting or removing protected health information from the object.

In some embodiments, the modification of the object may include reformatting the object into a new format.

In some embodiments, reformatting may include removing header information from the existing format and combining the header information with information from the record-side database into a new metadata file that is itself stored locally and linked to the object.

In some embodiments, modifying the object may include making a copy of the object, and performing the modification only on the copy of the object, leaving the original copy of the object in its original state.

In some embodiments, the API may include an integrated directory management system.

In some embodiments, the directory management system may include a visual query interface for filtering entity attributes contained within the record-side database ontology and pairing with associated objects recorded in the object side database.

In some embodiments, the results of the visual query interface may be displayed in a multi-level hierarchical format, and the order of the hierarchy may be set by the user in the visual query interface.

In some embodiments, the visual query interface may display a hierarchical structured view of mutually exclusive sets of selection attributes drawn from the data ontology, where the coarsest set of attributes for a comprehensively exhaustive set of attributes that define the provenance of source data and the structure of observational records and objects that form the source data, and where within the visual query interface the user may indicate the hierarchical order for presenting the results.

In some embodiments, the set of attributes displayed below the coarsest level may be drawn from key-value pairs defined within the database ontology.

Some embodiments of the present inventive concept provide an Application Programming Interface for managing the connection if image objects to database records, where the API includes methods and a user interface, where at least one method automatically constructs a database of metadata representative of the image objects and the user interface provides a graphical display of the contents of the image objects referenced in the database.

In some embodiments, the method for constructing the database may include creating and storing a coded name of the image object, creating a file object with additional metadata package relevant to interpretation of the image object, storing the file object in proximity to the image object, and providing a union of the image object and its metadata package with a mutual reference to the path of this object union, storing a path in the database to this object union.

In some embodiments, the method for constructing the database may include providing a coded link to a subject database to a subject, the subject database containing metadata relevant to the subject of the image object and the creation of the image object.

In some embodiments, the API user interface comprises an integrated directory management system.

In some embodiments, the directory management system includes a visual query interface for filtering entity attributes contained within the subject-side database ontology and pairing with associated objects recorded in the object side database.

In some embodiments, the results of the visual query interface are displayed in a multi-level hierarchical format, and the order of the hierarchy may be set by the user in the visual query interface.

In some embodiments, the visual query interface may display a hierarchical structured view of mutually exclusive sets of selection attributes drawn from the data ontology, where the coarsest set of attributes for a comprehensively exhaustive set of attributes, and where within the visual query interface the user may indicate the hierarchical order for presenting the results.

In some embodiments, the set of attributes displayed below the coarsest level may be drawn from key-value pairs defined within the database ontology.

Some embodiments of the present inventive concept provide a directory management system for visualizing and managing objects in a database or data lake according to a data ontology.

In some embodiments, the data ontology may be defined by a mutually exclusive and comprehensively exhaustive set of entities appropriate to a domain of data to be managed.

In some embodiments, the domain may be medical informatics, and the entities may include subjects, diagnosis codes, examiners, examination dates, and examination modalities.

In some embodiments, the domain may be medical informatics, and the entities may be subjects, research studies, diagnostic hypotheses, investigators, investigation dates, and investigation modalities.

In some embodiments, domain may be medical informatics, and the entities may include examination modalities, where examination modalities further include imaging or functional test modalities, where the imaging or functional test modalities contain further reference to the provenance of the test instruments, where the provenance to the test instruments includes the manufacturer and model of the test instrument.

In some embodiments, the provenance to the test instrument further comprises at least one of a set of instrument configurations and a set of instrument calibrations records appropriate to an examination.

In some embodiments, the entities may integrate a library of multiple disparate entities drawn from external sources, and where the external-drawn libraries include entities that standardize data definitions.

In some embodiments, the libraries may include one or more of a library of devices registered by a regulatory body and a library of common data elements defined by a domain-relevant data standards body. Note: this may include reference to FDA GUDID (Global Unique Device Identifier), GMDN (Global Medical Device Nomenclature), LOINC (Logical Observation Identifier Names and Codes), SNOMED, NIH CDE (Common Data Elements).

In some embodiments, the directory management system may include a visual organization structure, where the visible organization structure includes blocks of information directly drawn from and referenced to selected addressable entities of the data ontology.

In some embodiments, the addressable entities of the ontology may be selected programmatically as a subset of available entities from the ontology, which may be a complete set, through an Applications Programming Interface, and where the API may expose the full set or partial set of addressable entities through an executable program, a command line interface, or a graphical user interface.

In some embodiments, the addressable entities may be presented on a graphical user interface or accessible programmatically for down-selection, where down-selection comprises selecting a subset of addressable entities for organizing a collection of data, where the subset may be one, some, or all, of the addressable entities.

In some embodiments, the collection of down-selected addressable entities may be presented to the user on a display, where the user can multi-select one or more of the presented entities, where the selected entities are presented as individual blocks or panels on a user interface, where each individual panel includes one or more searchable attributes of the entity, where the user can multi-select one or more values of an attribute in each individual panel, and where the intersection of selected attributes of entities forms a complete query on the data in the database or data lake, and where a result of the query is made available to the user.

In some embodiments, a presentation of entity attributes may be constrained by a set of user permissions to allowable attributes, where allowable attributes are further constrained to be show actual values or coded values, such that a user may be blocked from seeing identifiable values that are forbidden according to the rules of the permission set.

In some embodiments, the values of data records or names of objects that are returned by the query may be constrained by the same set of user permissions, such that a user may be blocked from seeing identifiable values in data records or object names that are forbidden according to the rules of the permission set.

In some embodiments, the data contained within objects that are returned by the query may be constrained by the same set of user permissions, such that data contained with objects is redacted or coded, such that a user may be blocked from seeing identifiable values in with objects that are forbidden according to the rules of the permission set.

In some embodiments, the user may invoke one or more methods to operate on the results of the query.

In some embodiments, the method may include the renaming of objects returned by the query, where such renaming is defined by a template that includes components drawn from a selected attribute of the selected addressable entities.

In some embodiments, the template may be modified by the user within an API, where the query and the renaming template may be stored and recalled on demand or on a schedule, and where recall includes the updating of the results of the query based on changes to the database or data lake.

In some embodiments, the flexible directory management system may include the results of query on a subset of addressable entities and a subset of addressable values of such entities, where the set of addressable entities is defined within the API by reference to a data ontology, where the visibility of attributes may be constrained through coding or redaction according to a set of rules that set user permissions, where the names of objects returned by the query may be modified on display according to a template drawn from the ontology, addressable entities, and addressable values, where the naming convention is subject to the constraining set of rules.

In some embodiments, the results of the query may be organized in an exploded or indented hierarchy, where the levels of the hierarchy correspond to the selected addressable entities of the data ontology.

In some embodiments, the order of the hierarchy may be modified on demand in any of then n*(n−1) ordered combinations of any n selected addressable entities that form the basis of the query.

In some embodiments, the hierarchy may be displayed as a nested set of folders, where the folders are named according to the differentiated attribute of an entity, and where the objects returned in the query are in the lowest folder of the hierarchy, where if the lowest folder level in the hierarchy has a trivial contribution to the query, the objects returned in the query will reside in the lowest folder level with a non-trivial contribution to the query. As used herein, "trivial" refers to no further differentiation of data afforded by the query result defining the folder level.

In some embodiments, the directory management system may be set to display one or more views of resident objects according to the results of a specified query, in a hierarchical structure that corresponds to a subset of addressable entities within the ontology of the database or data lake, where the various views are available to the user according to the various demands of the user, subject to any rules and permissions that are established for viewing of the data and data objects.

In some embodiments, each hierarchical view of resident objects may provide a comprehensively exhaustive view of the available resident objects, subject to constraints of the rules and permissions.

In some embodiments, the methods may be non-destructive of the data and objects within the database or data lake, and where the history of invoked methods is recorded in an audit log.

The aforementioned flow logic and/or methods show the functionality and operation of various services and applications described herein. If embodied in software, each block may represent a module, segment, or portion of code that includes program instructions to implement the specified logical function(s). The program instructions may be embodied in the form of source code that includes human-readable statements written in a programming language or machine code that includes numerical instructions recognizable by a suitable execution system such as a processor in a computer system or other system. The machine code may be converted from the source code, etc. Other suitable types of code include compiled code, interpreted code, executable code, static code, dynamic code, object-oriented code, visual code, and the like. The examples are not limited in this context.

If embodied in hardware, each block may represent a circuit or a number of interconnected circuits to implement the specified logical function(s). A circuit can include any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Qualcomm® Snapdragon®; Intel® Celeron®, Core (2) Duo®, Core i3, Core i5, Core i7, Itanium®, Pentium®, Xeon®, Atom® and XScale® processors; and similar processors. Other types of multi-core processors and other multi-processor architectures may also be employed as part of the circuitry. According to some examples, circuitry may also include an application specific integrated circuit (ASIC) or a field programmable gate array (FPGA), and modules may be implemented as hardware elements of the ASIC or the FPGA. Further, embodiments may be provided in the form of a chip, chipset or package.

Although the aforementioned flow logic and/or methods each show a specific order of execution, it is understood that the order of execution may differ from that which is depicted. Also, operations shown in succession in the flowcharts may be able to be executed concurrently or with partial concurrence. Further, in some embodiments, one or more of the operations may be skipped or omitted. In addition, any number of counters, state variables, warning semaphores, or messages might be added to the logical flows or methods described herein, for purposes of enhanced utility, accounting, performance measurement, or providing troubleshooting aids, etc. It is understood that all such variations are within the scope of the present disclosure. Moreover, not all operations illustrated in a flow logic or method may be required for a novel implementation.

Where any operation or component discussed herein is implemented in the form of software, any one of a number of programming languages may be employed such as, for example, C, C++, C#, Objective C, Java, Javascript, Perl, PHP, Visual Basic, Python, Ruby, Delphi, Flash, or other programming languages. Software components are stored in a memory and are executable by a processor. In this respect, the term "executable" means a program file that is in a form that can ultimately be run by a processor. Examples of executable programs may be, for example, a compiled program that can be translated into machine code in a format that can be loaded into a random access portion of a memory and run by a processor, source code that may be expressed in proper format such as object code that is capable of being loaded into a random access portion of a memory and executed by a processor, or source code that may be interpreted by another executable program to generate instructions in a random access portion of a memory to be executed by a processor, etc. An executable program may be stored in any portion or component of a memory. In the context of the present disclosure, a "computer-readable medium" can be any medium (e.g., memory) that can contain, store, or maintain the logic or application described herein for use by or in connection with the instruction execution system.

A memory is defined herein as an article of manufacture and including volatile and/or non-volatile memory, removable and/or non-removable memory, erasable and/or non-erasable memory, writeable and/or re-writeable memory, and so forth. Volatile components are those that do not retain data values upon loss of power. Nonvolatile components are those that retain data upon a loss of power. Thus, a memory may include, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may include, for example, static random access memory (SRAM), dynamic random access memory (DRAM), or magnetic random access memory (MRAM) and other such devices. The ROM may include, for example, a programmable read-only memory (PROM), an erasable programmable read-only memory (EPROM), an electrically erasable programmable read-only memory (EEPROM), or other like memory device.

The devices described herein may include multiple processors and multiple memories that operate in parallel processing circuits, respectively. In such a case, a local interface, such as a communication bus, may facilitate communication between any two of the multiple processors, between any processor and any of the memories, or between any two of the memories, etc. A local interface may include additional systems designed to coordinate this communication, including, for example, performing load balancing. A processor may be of electrical or of some other available construction.

It should be emphasized that the above-described embodiments of the present disclosure are merely possible examples of implementations set forth for a clear understanding of the principles of the disclosure. It is, of course, not possible to describe every conceivable combination of components and/or methodologies, but one of ordinary skill in the art may recognize that many further combinations and permutations are possible. That is, many variations and modifications may be made to the above-described embodiment(s) without departing substantially from the spirit and principles of the disclosure. All such modifications and variations are intended to be included herein within the scope of this disclosure and protected by the following claims.

That which is claimed is:

1. An application programming interface (API) resident on a computer that, upon receiving a message that a data set associated with an encounter experienced by a subject is available, causes a processor to:
   read a structured file associated with the data set, the structured file having a set of records assigned to a subset of pre-defined fields and a location of one or more unstructured objects, the pre-defined fields being organized according to an ontology having at least records related to the subject, the encounter and the data set; and
   populate at least first and second independent and distinct relational databases using endpoints of the API, the first relational database including records related to the one or more unstructured objects and excluding records associated with the subject and the encounter and the second relational database including records associated with the subject and the encounter, wherein a schema of the second relational database includes at least a first addressable table that includes protected data associated with the subject and the encounter and at least a second addressable table that excludes protected data associated with the subject and the encounter;

wherein a set of addressable processes of the API are invoked to export one or more of:

unstructured objects and structured data about objects from the first relational database, the structured data being completely absent of records associated with the subject and the encounter;

unstructured objects and structured data about objects from the first and/or second relational databases, the structured data including records associated with the encounter but being completely absent of records associated with the subject; and unstructured objects and structured data about objects from the first and/or second relational databases, the structured data including records associated with the subject and the encounter.

2. The API of claim 1, wherein the API is invoked to search, manipulate and/or share data in the first relational database without concern for confidentiality related to revealing personal data associated with the subject or the encounter.

3. The API of claim 1, wherein the API is invoked to restore data stored in the first relational database into patient specific data when accessed by authorized personnel.

4. The API of claim 1, wherein the API operates between the first and second relational databases allowing authorized communication therebetween.

5. The API of claim 1, wherein the API is integrated within an imaging system.

6. The API of claim 1, wherein the API comprises a user interface allowing access thereto and a directory manager including rules, permissions, methods and logs.

7. The API of claim 1, wherein data files are stored having an original name associated therewith in a code not accessible by a user of the API and wherein the data files are relabeled based on user preferences leaving the original name intact.

8. The API of claim 1, wherein the API is invoked by system software of a device, the API is read for data in a target storage location and/or the API is invoked periodically using a scheduler.

9. The API of claim 1, wherein the API is invoked to automatically create a structured file object by combining structured records stored in tagged files with one or more of the unstructured file or image objects in the first and/or second relational databases.

10. The API of claim 1, wherein the API is invoked to convert data obtained and stored in a first format to a distinctly different format.

11. The API of claim 10, wherein data exported via the API is consumable by a third independent and distinct relational database that shares a common ontology regardless of origin of the data.

12. The API of claim 1, wherein the API is invoked to automatically publish source data to digital imaging and communication (DICOM) conformant files independent of source of metadata associated with the source data or the format source object.

13. The API of claim 1, wherein the first relational database includes records related to the one or more unstructured objects that have been completely stripped of all protected health information (PHI) associated with the subject and the encounter and wherein the second relational database includes records associated with the subject and the encounter including any relevant PHI.

14. The API of claim 1, wherein invoking the API causes the API to automatically populate the first relational database and wherein the first relational database includes a coded-link between each object therein and a unique event linked to a subject in second relational database.

15. The API of claim 1, wherein automatically populating the first relational database comprises:

searching a target data lake for objects that match results of a query initiated from the second relational database;

identifying an object in the target data lake;

automatically populating a storage path identifier for the object into the first relational database; and returning to the second relational database a key that links a subject record in the second relational database to the object record in the first relational database.

16. The API of claim 15, wherein populating the first relational database comprises populating the first relational database with additional records descriptive of an object drawn from the data lake, including one or more of a file type, a file size, a file creation date and time stamp.

17. The API of claim 15, wherein populating the relational database comprises populating the first relational database with additional records descriptive of an object that is drawn from a record, including one or more of an activity type that defines an event creating the object, an anatomy or component of a subject that is the subject of the object, a gender of the subject, an age of the subject at a time of the object curation, a pathological diagnosis or condition of the subject at a time of object creation, a method type that defines creation of the object, a hardware definition that defines equipment used to generate the object, a configuration set that defines operating conditions at use in the creation of the object and a calibration set that provides for quantitative interpretation of the object.

18. The API of claim 1, wherein the API includes processes and a user interface, where at least one method automatically constructs a database of metadata representative of image objects and the user interface provides a graphical display of contents of the image objects referenced in the database.

19. An imaging system comprising an application programming interface (API) resident on a computer that, upon receiving a message that a data set associated with an encounter experienced by a subject is available, causes a processor to:

read a structured file associated with the data set, the structured file having a set of records assigned to a subset of pre-defined fields and a location of one or more unstructured objects, the pre-defined fields being organized according to an ontology having at least records related to the subject, the encounter and the data set; and populate at least first and second independent and distinct relational databases using endpoints of the API, the first relational database including records related to the one or more unstructured objects and excluding records associated with the subject and the encounter and the second relational database including records associated with the subject and the encounter, wherein a schema of the second relational database includes at least a first addressable table that includes protected data associated with the subject and the encounter and at least a second addressable table that excludes protected data associated with the subject and the encounter;

wherein a set of addressable processes of the API are invoked to export one or more of:

unstructured objects and structured data about objects from the first relational database, the structured data being completely absent of records associated with the subject and the encounter;

unstructured objects and structured data about objects from the first and/or second relational databases, the structured data including records associated with the encounter but being completely absent of records associated with the subject; and unstructured objects and structured data about objects from the first and/or second relational databases, the structured data including records associated with the subject and the encounter.

* * * * *